(12) United States Patent
Lyczak et al.

(10) Patent No.: US 8,425,880 B1
(45) Date of Patent: Apr. 23, 2013

(54) METAL-CONTAINING MATERIALS FOR TREATMENT OF BACTERIAL CONDITIONS

(75) Inventors: Jeffrey B. Lyczak, Malden, MA (US); Katherine Thompson, Andover, MA (US); Katherine Turner, Acton, MA (US); Paul Schechter, Dover, MA (US)

(73) Assignee: Nucryst Pharmaceuticals Corp., Fort Saskatchewan, Alberta (CA)

( * ) Notice: Subject to any disclaimer, the term of this patent is extended or adjusted under 35 U.S.C. 154(b) by 1360 days.

(21) Appl. No.: 12/109,897

(22) Filed: Apr. 25, 2008

Related U.S. Application Data

(60) Provisional application No. 60/979,239, filed on Oct. 11, 2007, provisional application No. 60/972,501, filed on Sep. 14, 2007, provisional application No. 60/915,604, filed on May 2, 2007.

(51) Int. Cl.
*A61K 49/00* (2006.01)
*A61K 33/24* (2006.01)
*A01N 25/00* (2006.01)

(52) U.S. Cl.
USPC ............ 424/9.2; 424/9.1; 424/405; 424/408; 424/417; 424/604; 424/617; 424/618; 424/234.1; 424/239.1; 424/246.1

(58) Field of Classification Search .................. 424/9.1, 424/9.2, 405, 408, 417, 604, 617, 618, 234.1, 424/239.1, 246.1
See application file for complete search history.

(56) References Cited

U.S. PATENT DOCUMENTS

| | | | |
|---|---|---|---|
| 5,958,440 A | 9/1999 | Burrell et al. | |
| 6,277,414 B1 | 8/2001 | Elhaik et al. | |
| 6,827,766 B2 * | 12/2004 | Carnes et al. | 106/15.05 |
| 2002/0022012 A1 * | 2/2002 | Cooper et al. | 424/78.17 |

OTHER PUBLICATIONS

International Search Report and Written Opinion for international application No. PCT/US2008/061597, dated Apr. 15, 2010.

\* cited by examiner

*Primary Examiner* — Rodney P. Swartz
(74) *Attorney, Agent, or Firm* — Fish & Richardson P.C.

(57) ABSTRACT

Metal-containing materials, as well as their preparation, formulations, and use are disclosed.

45 Claims, 4 Drawing Sheets

METAL-CONTAINING MATERIALS FOR TREATMENT OF BACTERIAL CONDITIONS

CROSS-REFERENCE TO RELATED APPLICATIONS

This application claims the benefit of the filing date of U.S. Provisional Patent Application Ser. No. 60/915,604, filed May 2, 2007; U.S. Provisional Patent Application Ser. No. 60/972,501, filed Sep. 14, 2007; and U.S. Provisional Patent Application Ser. No. 60/979,239, filed Oct. 11, 2007, the contents of which are hereby incorporated by reference.

TECHNICAL FIELD

The disclosure relates to metal-containing materials, as well as formulations and uses thereof.

BACKGROUND

A variety of gastrointestinal pathological conditions in humans can be attributed, in total or in part, to micro-organisms, to inflammatory processes, or to a combination of both. For example, *Clostridium difficile* can cause pseudomembranous colitis, and can account for approximately 25% of cases of antibiotic-associated diarrhea, with an overall frequency of over 500 cases per 100,000 patients—a frequency which has risen markedly over the past decade. Risk factors and/or individuals susceptible for *C. difficile*-Associated Disease (CDAD) include extended hospitalization, advanced age, exposure to any of a number of antibiotics, immuno-suppressed individuals, individuals having IBD, individuals having CDAD or having had CDAD, and/or individuals undergoing chemotherapy. CDAD can be treated by discontinuation of the initiating antibiotic and administration of either vancomycin or metronidazole, both of which are highly effective. However, while treatment with antibiotic medication such as metronidazole and/or vancomycin can be effective against CDAD, treatment with both these agents is associated with about 20% rate of relapse. Additionally, the use of vancomycin is restricted due to concerns about vancomycin-resistant enterococci.

As another example of gastrointestinal pathological conditions, *Helicobacter pylori* is associated with a majority of peptic ulcers, and is implicated in gastritis and in gastric malignancies. As further examples, *Shigella dysenteriae*, *Shigella flexneri*, enterophathogenic *Escherichia coli*, *Staphylococcus aureus*, *Enterococcus faecalis*, *Enterococcus faecium*, *Salmonella enterica*, *Campylobacter jejunum*, *Clostridium perfringens*, *Bacillus cereus*, *Vibrio cholera*, *Vibrio parahaemolyticus*, and *Giardia lamblia* are enteric micro-organisms which can cause diarrhea, dysentery, and severe intestinal disease.

SUMMARY

The disclosure relates to metal-containing materials, as well as their preparation and use.

In one aspect, the disclosure features a method including contacting an area of a subject having bacterial spores with one or more silver-containing materials to kill the bacterial spores.

In another aspect, the disclosure features an article including a bead including from 0.01 to 20 percent by weight of one or more metal-containing materials; and a controlled-release coating.

Embodiments can include one or more of the following features.

In some embodiments, the bacterial spores include *Clostridium difficile* spores, *Clostridium perfringens* spores, *Clostridium tetani* spores, *Clostridium botulinum* spores, *Bacillus cereus* spores, and/or *Bacillus anthracis* spores.

In some embodiments, the area of the subject further includes a bacterial infection. The bacterial infection can include a *Clostridium* infection, such as *Clostridium difficile* infection, *Clostridium perfringens* infection, *Clostridium tetani* infection, and/or *Clostridium botulinum* infection. In certain embodiments, the bacterial infection includes a *Clostridium difficile* infection. In some embodiments, the bacterial infection includes a *Bacillus* infection, such as a *Bacillus cereus* infection and/or a *Bacillus anthracis* infection.

In some embodiments, the area includes an oral cavity, a gastrointestinal tract, a nasal cavity, a respiratory tract, an ulceration, a connective tissue, and/or a wound.

In some embodiments, the one or more silver-containing materials are bactericidal and/or sporicidal. The one or more silver-containing materials can include silver, silver oxide, silver nitrate, an atomically disordered silver-containing material and/or nanocrystalline silver.

In some embodiments, contacting the area with one or more silver-containing materials includes oral administration, inhalation, rectal administration, and/or topical administration of the one or more silver-containing materials. In some embodiments, the method further includes contacting the area with one or more non-metal antibiotic medications. The one or more non-metal antibiotic medications can include vancomycin, metronidazole, benzoxazinorifamycin, and/or rifaximin. The one or more non-metal antibiotic medications can be contacted to the area before, after, or simultaneous with contacting the area with the one or more silver-containing materials.

In some embodiments, the one or more silver-containing material is contacted with the area at a dose of from 0.1 to 1000 mg/kg or from 0.1 to 10,000 mg, and/or at a frequency of from one to four times per day. In some embodiments, the non-metal antibiotic medication is contacted with the area at a dose of from 50 to 4000 mg/kg or from 50 to 4000 mg, and/or at a frequency of from one to four times per day.

In some embodiments, the one or more silver-containing materials includes a controlled-release composition (e.g., a composition having controlled-release properties, a coated controlled-release composition, an enteric composition, an enteric-coated composition), a solution, a nanodispersion, an aerosol, a cream, and/or a gel. The controlled-release composition can include a suspension, a capsule, a tablet, and/or a pill. In some embodiments, the controlled-release composition includes a bead that includes from 0.01 to 20 percent by weight of the one or more silver-containing materials. The bead can be coated with the one or more silver-containing material and/or a controlled-release coating. The bead can include sugar or starch. The bead can have a maximum average dimension of from 0.5 to 2 mm.

In some embodiments, the article can include a suspension, a capsule, a tablet, and/or a pill. The article can include one or more metal-containing materials, such as an atomically disordered metal-containing material, and/or an atomically disordered, nanocrystalline metal-containing material. In some embodiments, the article including the one or more metal-containing material can include silver-containing materials, gold-containing materials, platinum-containing materials, palladium-containing materials, copper-containing materials, and/or zinc-containing materials. For example, the one or more metal-containing materials can include nanocrystalline silver, and/or an atomically disordered, nanocrystalline silver. As an example, the one or more metal-containing materials can include silver oxide.

In some embodiments, the article includes from 0.01 to 20 percent by weight of the controlled-release coating, which can include beeswax, beeswax and glyceryl monostearate, shellac and cellulose, cetyl alcohol, mastic and shellac, shellac and stearic acid, polyvinyl acetate and ethyl cellulose, neutral copolymer of polymethacrylic acid ester (Eudragit L30D), copolymer of methacrylic acid and methacrylic acid methylester (Eudragits), neutral copolymers of polymethacrylic acid esters containing metallic stearates, and/or neutralized hydroxypropyl methylcellulose phthalate polymer.

Embodiments can include one or more of the following advantages.

In some embodiments, the metal-containing material is both sporicidal and bactericidal. Hence, the metal-containing material can kill both the bacteria and bacterial spores of an infected area, and can thereby decrease the likelihood of recurrence of a bacterial infection by decreasing the number of viable spores. In some embodiments, the metal-containing material can interfere with germination of the bacterial spores. In some embodiments, infection of an area of a subject does not occur within a year (e.g., within six months, within three months, or within one month) of a conclusion of treatment with a therapeutic agent, such as a metal-containing material, or a metal-containing material and a non-metal antibiotic medication. In some embodiments, a combination treatment with a metal-containing material and a non-metal antibiotic medication is more effective in killing bacteria and bacterial spores than a treatment with either a metal-containing material or a non-metal antibiotic medication. In some embodiments, continuous or intermittent treatment including a metal-containing material is less likely to result in resistant strains of bacteria and/or bacterial spores over a period of time (e.g., greater than three months, greater than six months, greater than one year, greater than two years) than a treatment without a metal-containing material (e.g., with an non-metal antibiotic medication).

In some embodiments, the composition including the metal-containing material can be easily processed and manufactured. The composition can be well-tolerated by a subject and/or can be non-irritating. In some embodiments, the composition (e.g., a cream) is an anti-microbial barrier. The composition can be anti-inflammatory.

Other features, objects, and advantages of the methods and compositions will be apparent from the description and drawings, and from the claims.

DETAILED DESCRIPTION

Figure 1:
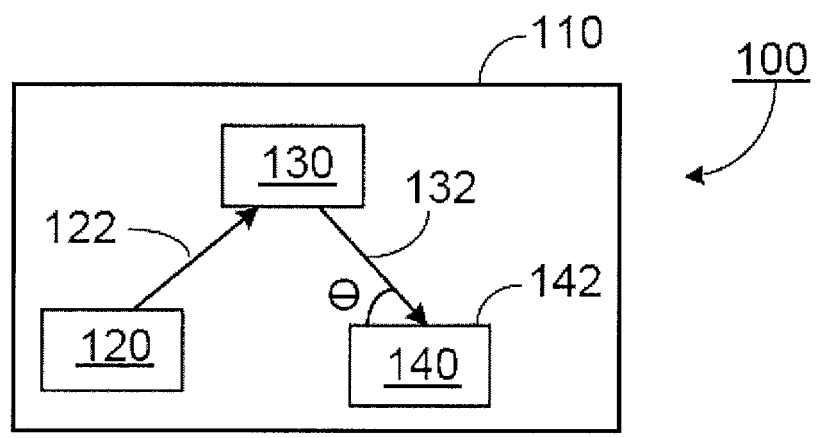
FIG. 1 is a schematic view of a deposition system.
Figure 2:
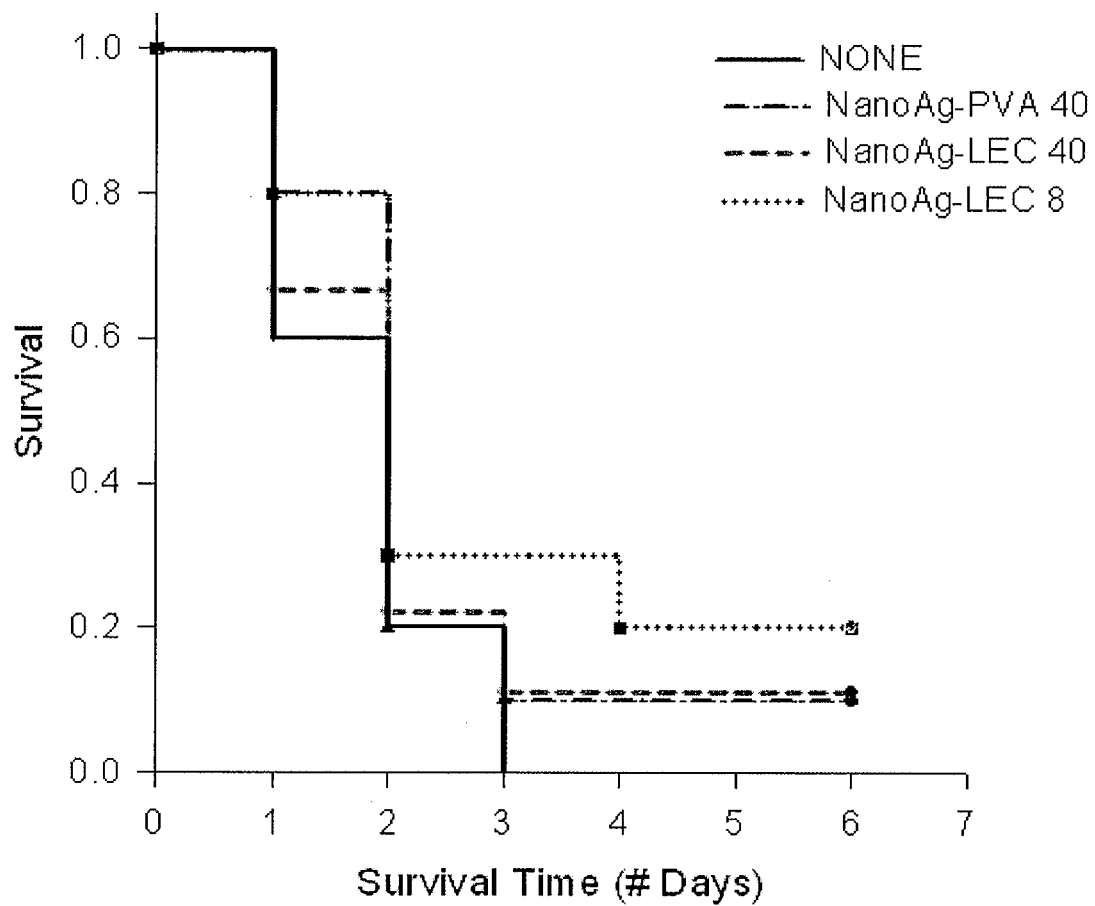
FIG. 2 is a graph showing the survival of hamsters treated orally with nanocrystalline silver (Nano-Ag), after colonization with *C. difficile* ATCC 43600. The treatment groups were: untreated (NONE), or nanocrystalline silver dispersions with polyvinyl alcohol (PVA) or lecithin (LEC) used as dispersant. Nanocrystalline silver dispersions were given at doses of 40 or 8 mg/kg/day. Each set of test conditions was tested with ten hamsters.
Figure 3:
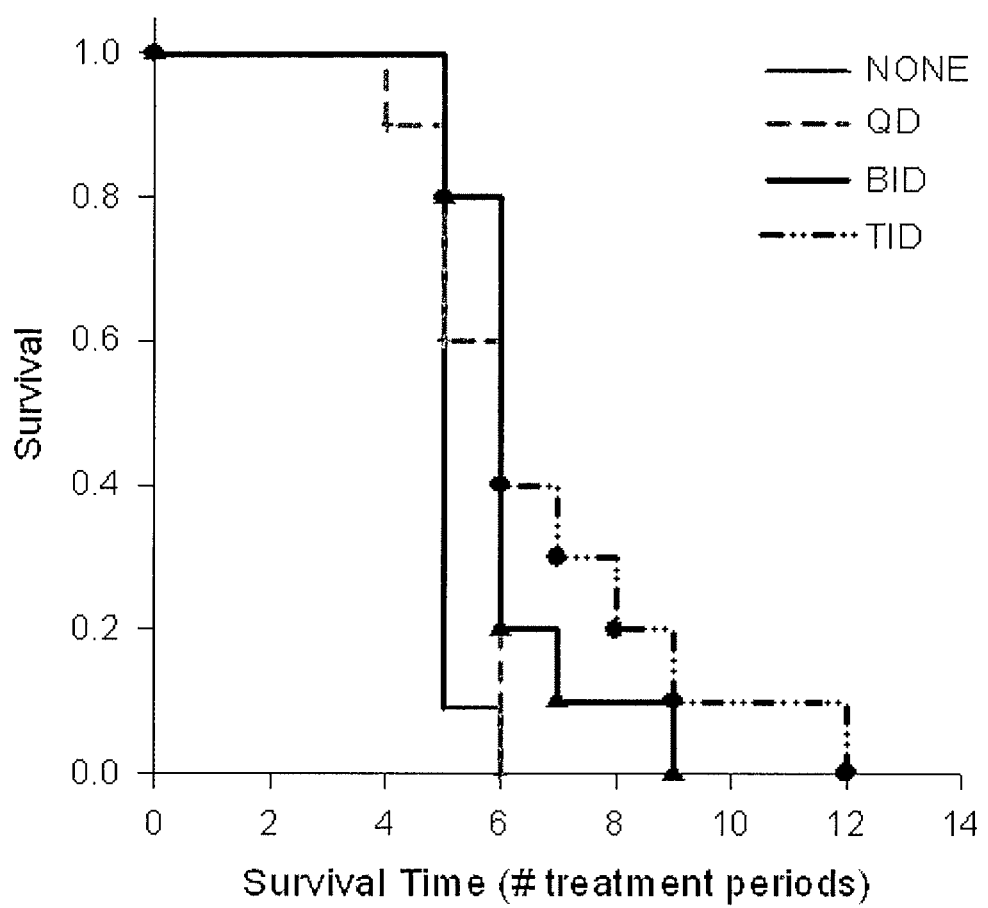
FIG. 3 is a graph showing the survival of hamsters treated orally by different doses and schedules with nanocrystalline silver in a lecithin dispersion after colonization with *C. difficile* ATCC 43600. The treatment groups were: untreated (NONE), or receiving Nano-Ag Lecithin once per day (QD; 16 mg/kg/day), twice per day (BID; 32 mg/kg/day), or three times per day (TID; 48 mg/kg/day). Each set of test conditions was tested with ten hamsters.
Figure 4:
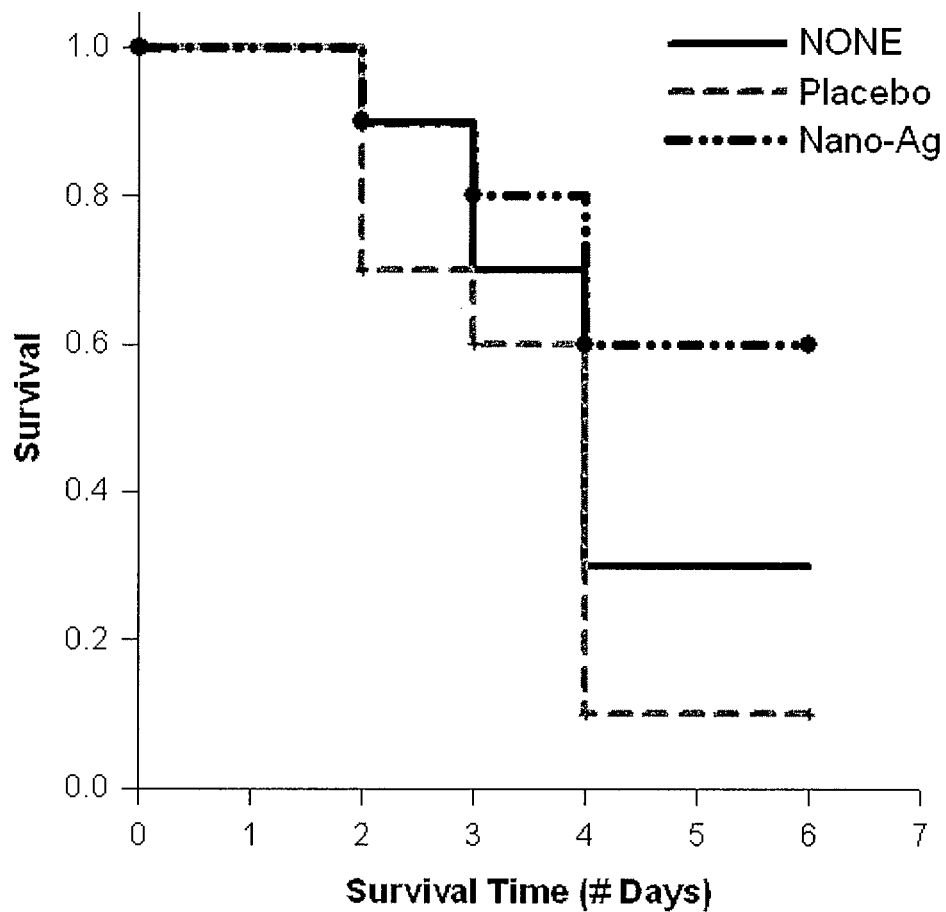
FIG. 4 is a graph showing the survival of hamsters treated with nano-Ag before clindamycin administration and naturally-acquired colonization. The groups were: untreated (NONE), or once a day treatment with either nanocrystalline silver in lecithin (16 mg/kg/day) or an equal volume of lecithin placebo. Each set of test conditions was tested with ten hamsters.

Certain metal-containing materials (e.g., antimicrobial, anti-inflammatory, atomically disordered, and/or nanocrystalline silver-containing materials) can be used to treat a subject by contacting an area of the subject having a condition with one or more metal-containing materials. The area of the subject having the condition can have bacteria and/or bacterial spores, and the metal-containing material(s) can kill the bacteria and bacterial spores. As explained below, the condition can be any of a variety of conditions, the metal-containing material can be in any of a variety of forms when delivered to a subject, and the metal-containing material can be delivered to a subject in a variety of ways.

Suitable conditions that can be treated with the metal-containing material (e.g., one or more metal-containing materials) include conditions having bacteria and/or bacterial spores. In some embodiments, the conditions can be caused by or aggravated by the bacteria and/or bacterial spores. The bacteria can be sporulating bacteria. The bacteria and the bacterial spores can be of the same species. For example, the conditions can include CDAD, tetanus, botulism, gas gangrene, anthrax infection, toxic shock syndrome, and/or opportunistic infections. Without wishing to be bound by theory, it is believed that bacterial infections caused by sporulating bacteria can often recur even after treatment with conventional antibiotic medicament, because bacterial spores can survive treatment even when bacteria are killed by the antibiotic medicament. Hence, once the antibiotic medicament is cleared from a subject, the bacteria spores can germinate into bacteria and re-establish the bacterial infection in the subject. In some embodiments, metal-containing materials of the present disclosure are advantageous because of their bactericidal and sporicidal properties, as the metal-containing materials can kill both the bacteria and bacterial spores of an infected area, and thereby decrease the likelihood of recurrence of a bacterial infection by decreasing the number of viable spores. Further, as the occurrence of bacteria and/or bacterial spore resistance to metal-containing material is unlikely, the use of metal-containing materials can be beneficial in conditions having multiple relapses, when extended treatment can be involved.

In some embodiments, the bacteria and/or bacterial spores can include species of the *Clostridium* genus, such as *C. difficile*, *C. perfringens*, *C. tetani*, and/or *C. botulinum*. In some embodiments, the bacteria/bacterial spores can include spores of the *Bacillus* genus, such as *B. cereus* and/or *B. anthracis*.

In some embodiments, the metal-containing materials are bactericidal against a wide variety of bacteria. In some embodiments, when a metal-containing material is effective in killing a representative species of a given bacterial genus, the metal-containing materials is effective against other species within the given bacterial genus or a different bacterial genus (e.g., the *Clostridium* genus, the *Bacillus* genus). In some embodiments, a metal-containing material that is effective in killing *B. cereus* can also be effective against *B. anthracis*. In some embodiments, a metal-containing material that is effective in killing *C. difficile* is also effective in killing *C. perfringens, C. tetani*, and/or *C. botulinum.*

The area of the subject having bacteria and/or bacterial spores can vary depending on the species of the bacteria and/or bacterial spores. For example, *C. difficile* bacteria and spores can be found in a gastrointestinal tract (e.g., the intestines); *C. perfringens* bacteria and spores can be found in a gastrointestinal tract, a connective tissue, a wound, and/or in an area having gas gangrene; and *C. tetani* bacteria and spores can be found in a wound. In some embodiments, *Bacillus* bacteria and spores (e.g., *B. anthracis* and/or *B. cereus*) can be found in a respiratory airway, a wound, an area of the skin, a blood stream, and/or in the gastrointestinal tract. In some embodiments, the wound is in an area of the skin or a soft tissue. In some embodiments, a bacterial infection can include a systemic component. For example, while gas gangrene and tetanus can both be superficial infections (e.g., gas gangrene can result from an infected ulcer on an area of the skin and tetanus from an infected puncture wound). In some embodiments the bacterial infection can spread throughout the body (e.g., gas gangrene), and/or the localized bacterial infection can produce a toxin that is circulated in a subject (e.g., tetanus).

In some embodiments, the area of a subject affected with a condition having bacteria and/or bacterial spores is treated with a therapeutically effective amount of one or more metal-containing materials. Treatment can continue until the condition ameliorates or disappears. As used herein, a therapeutically effective amount refers to an amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptoms of the disease; or decreasing the likelihood of a relapse of a disease, condition, or disorder in an individual;

(2) inhibiting the disease; for example, inhibiting a disease, condition or disorder in an individual who is experiencing or displaying the pathology or symptoms of the disease, condition or disorder (i.e., arresting further development of the pathology and/or symptoms) such as lowering the bacterial load in the case of a bacterial infection, and (3) ameliorating the disease; for example, ameliorating a disease, condition or disorder in an individual who is experiencing or displaying the pathology or symptoms of the disease, condition or disorder (i.e., reversing the pathology and/or symptoms) such as reducing infection-related tissue damage in the case of a bacterial infection.

The metal-containing material can be contacted to an area in a variety of forms. For example, a dressing containing an appropriate metal-containing material (e.g., antimicrobial, atomically disordered, silver-containing material) can be applied to an area of the skin having a condition. As another example, a controlled-release composition containing an appropriate metal-containing material can be contacted with an area (e.g., a gastrointestinal area) having a condition, by ingesting the controlled-release composition. As another example, an aerosol containing an appropriate metal-containing materials can be contacted with an area (e.g., a respiratory area) having a condition, by breathing in the aerosol. As a further example, a metal-containing material can be contacted with the area having a condition (e.g., a systemic condition) by injecting a solution including a metal-containing material.

Moreover, while the foregoing has described embodiments that involve one method of contacting a subject with the metal-containing material, in other embodiments, more than one method of contacting a subject with the metal-containing material can be used. For example, the methods can include one or more of ingestion (e.g., oral ingestion), injection (e.g., using a needle, using a needleless injector), topical administration, inhalation (e.g., inhalation of a dry powder, inhalation of an aerosol) and/or application of a dressing. The methods for application of a metal-containing material to the subject can vary in a number of ways, generally depending upon the form of the material as applied and/or the location of the condition to be treated. In general, the amount of material used is selected so that the desired therapeutic effect (e.g., reduction in the condition being treated) is achieved while the material introduces an acceptable level of toxicity (e.g., little or no toxicity) to the subject. Generally, the amount of the material used will vary with the conditions being treated, the stage of advancement of the condition, the age and type of host, and the type, concentration and form of the material as applied. In some embodiments, a single application of the material may be sufficient. In certain embodiments, the material may be applied repeatedly over a period of time, such as several times a day for a period of days, weeks, months or years.

Furthermore, while the foregoing has described embodiments in which one form of the metal-containing material is used, in other embodiments, more than one form of the metal-containing material can be used. For example, the methods can include using the metal-containing material in the form of a controlled-release composition, a coating (e.g., a dressing), a free standing powder, a freeze-dried powder, a solution and/or a pharmaceutical carrier composition.

In some embodiments, the metal-containing material can be used in various settings having relatively high exposure to bacterial infections and/or relatively high human contact. For example, the metal-containing material can be used in a hospital setting. The metal-containing material can be used to reduce and/or prevent bacterial/bacterial spore growth on surfaces (e.g., hands, hospital equipment, office equipment). In some embodiments, the metal-containing material is disposed in a hand sanitizer, or in a disinfectant spray, and can be applied to a surface of interest to reduce and/or prevent bacterial/bacterial spore growth.

Moreover, the metal-containing material can be used in various industrial applications. For example, the metal-containing material can be used to reduce and/or prevent microbial growth on industrial surfaces (e.g., industrial surfaces where microbial growth may occur, such as warm and/or moist surfaces). Examples of industrial surfaces include heating pipes and furnace filters. In certain embodiments, the metal-containing material can be disposed (e.g., coated or sprayed) on the surface of interest to reduce and/or prevent microbial growth. This can be advantageous in preventing the spread of microbes via, for example, heating and/or air circulation systems within buildings.

Treatment with One or More Metal-Containing Materials

In general, treatment and/or inhibition of conditions having bacteria/bacterial spores involves contacting the metal-containing material with the area of the body having the condition. As an example, a condition can be inhibited and/or treated by contacting the area having the condition with a controlled-release composition, a coating (e.g., a dressing), a free standing powder, a freeze-dried powder, a solution and/or a pharmaceutical carrier composition containing the metal-containing material.

In some embodiments, treatment and/or inhibition of conditions can involve contacting the metal-containing material with the area of the body having the condition in combination with one or more non-metal antibiotic medications. Examples of non-metal antibiotic medications include vancomycin, metronidazole, benzoxazinorifamycin, and/or rifaximin. Treatment with the non-metal antibiotic medications different from the metal-containing material can occur before, after, or simultaneously with treatment with metal-containing material. The non-metal antibiotic medication can be administered to a subject in a variety of ways that can be the same as or different from the anti-microbial material.

The dose when using the metal-containing material and/or the non-metal antibiotic medication can vary within wide limits, and as is customary and is known to the physician, it is to be tailored to the individual conditions in each individual case. It depends, for example, on the nature and severity of the illness to be treated, on the condition of the patient, on the therapeutic agent(s) employed or on whether an acute or chronic disease state is treated or prophylaxis is conducted or on whether further therapeutic agents are administered in addition to the metal-containing material and/or non-metal antibiotic medication. Representative doses of the metal-containing material and/or the non-metal antibiotic medication are described below. Depending on the individual and as deemed appropriate from the patient's physician or care-giver it may be necessary to deviate upward or downward from the doses described herein.

In some embodiments, the metal-containing material is administered at a dose of from 0.05 milligram (mg) to 1.5 gram (g) (e.g., from 0.1 mg to 1.0 g, from 0.1 g to 0.5 g, or from 0.5 g to 1.0 g). In some embodiments, the metal-containing material is administered at a dose of at least 0.05 mg (e.g., at least 0.1 mg, at least 100 mg, at least 500 mg, or at least 800 mg) and/or at most 1.5 g (e.g., at most one gram, at most 800 mg, at most 500 mg, at most 100 mg, or at most 0.1 mg).

In some embodiments, the non-metal antibiotic medication is administered at a dose of from 40 mg to four grams (e.g., from 100 mg to three grams, from 100 mg to two grams, from one to two grams). In some embodiments, the non-metal antibiotic medication is administered at a dose of at least 40 mg (e.g., at least 100 mg, at least 500 mg, at least one gram, at least two grams, or at least three grams) and/or at most four grams (e.g., at most three grams, at most two grams, at most one gram, at most 500 mg, or at most 100 mg).

In some embodiments, the metal-containing material and/or non-metal antibiotic medication can be administered to a subject (e.g., a human subject) at a frequency of at least one dose per day (e.g., at least one dose per 12 hours, or at least one dose per 6 hours) and/or at most one dose per three hours (e.g., at most one dose per six hours, or at most one dose per 12 hours). In some embodiments, the metal-containing material and/or non-metal antibiotic medication are administered to a subject (e.g., a human subject) at a frequency of from one dose per day to one dose per three hours (e.g., from one dose per day to one dose per six hours, from one dose per day to one dose per 12 hours). The metal-containing material and/or non-metal antibiotic medication can contact the area continuously, or for a duration of about one hour per dose (e.g., about a half hour per dose, about 15 minutes per dose, about five minutes per dose, about one minute per dose).

In some embodiments, a treatment cycle with the metal-containing material and/or the non-metal antibiotic medication can last at least one day (at least three days, at least one week, or at least two weeks) and/or at most one month (e.g., at most two weeks, at most one week, or at most three days). In some embodiments, a treatment cycle with the metal-containing material and/or the non-metal antibiotic medication can last from one day to two months (e.g., from one day to one month, from one day to two weeks, from one day to one week, or from one to three days). As used herein, a treatment cycle refers to length of time at which the active compound or pharmaceutical agent achieves the biological or medicinal response that is being sought in a tissue, system, animal, individual or human by a researcher, veterinarian, medical doctor or other clinician.

In some embodiments, when the condition having bacteria and/or bacterial spores is treated with the metal-containing material in conjunction with an non-metal antibiotic medication, the treatment cycle with the metal-containing material can start at the same time as, before, and/or after a treatment cycle with the non-metal antibiotic medication. In some embodiments, the treatment cycle with the metal-containing material overlaps with the treatment cycle with an non-metal antibiotic medication. For example, the treatment cycle with the metal-containing material at a prescribed dose and frequency can start at most a month (e.g., at most two weeks, at most a week, at most three days, or at most a day) and/or at least a day (at least three days, at least a week, or at least two weeks) in advance of, or after, the start of a treatment cycle with the non-metal antibiotic medication.

In some embodiments, when the condition having a bacteria and/or a bacterial spores is treated the metal-containing material in conjunction with one or more non-metal antibiotic medications, delivery of each dose of the metal-containing material can occur at the same time as, before, or after delivery of a dose of non-metal antibiotic medication. The doses of the metal-containing material and the non-metal antibiotic medication can be the same or different. The dose delivery frequency of the metal-containing material and the non-metal antibiotic medication can be the same or different.

Microbial Conditions

In some embodiments, the condition is a microbial condition including sporulating bacteria, which includes certain Gram-positive bacteria. An antibiotic-resistant bacterium refers to a bacterium whose growth and reproduction is unaffected by particular non-metal antibiotics such as methicillin and/or vancomycin. Examples of microbial conditions including sporulating bacterial included CDAD, anthrax, botulism, gas gangrene, tetanus, toxic shock syndrome, and/or opportunistic bacterial infections.

In some embodiments, the microbial conditions are characterized by the presence of bacterial (e.g., sporulating bacteria) biofilms. A biofilm is a complex aggregation of bacteria, which secrete a protective and adhesive matrix. Biofilms can attach to a surface, and exhibit structural heterogeneity, genetic diversity, complex community interactions, and an extracellular matrix of polymeric substances. Biofilm conditions can be the cause of persistent and chronic infections, and can affect a variety of tissues such as the gum and jawbone (periodontal tissue), the eye (e.g., infection by contact lenses having biofilms), the lung (e.g., chronic lung infections), the gastrointestinal tract, internal tissue (e.g., endocarditis) and the skin (e.g., infected skin, infected burn wounds). Biofilms can also form on medical devices implanted in the body such as catheters and heart valves, or on contact lenses.

In general, treatment and/or inhibition of microbial conditions involves contacting the metal-containing material with the area of the body having the condition. As an example, a microbial condition can be inhibited and/or treated by contacting the area having the condition with a formulation such as a controlled-release composition, a cream, a foam, a gel, a lotion, a paste, an ointment, a nanodispersion, and/or a solution containing the metal-containing material.

In some embodiments, the microbial condition can be treated and/or prevented by contacting the metal-containing material with the area of the body or device having a microbial condition and/or susceptible to the formation of a microbial condition. As an example, a microbial condition (e.g., a biofilm condition) can be treated and/or prevented by contacting or coating the susceptible area or device with a formulation such as a controlled-release composition, a cream, a foam, a gel, a lotion, a paste, an ointment, a nanodispersion, and/or a solution containing the metal-containing material. In some embodiments, for an internal administration, the formulation can have a metal-containing material administered at a metal dosage of at least 0.1 mg of a metal-containing material per one kg of a subject (e.g., at least 0.4 mg/kg, at least 40 mg/kg, or at least 400 mg/kg) and/or at most 1000 mg/kg (e.g., at most 400 mg/kg, at most 40 mg/kg, or at most 0.4 mg/kg), and for a period sufficient to treat/alleviate/cure the condition. For example, the metal dosage can be from 0.1 to 10,000 mg (e.g., e.g., from 0.1 to 5,000 mg, from 0.1 to 1,000 mg, from 0.4 to 1000 mg, from 0.4 to 400 mg, from 0.4 to 40 mg, from 40 to 400 mg) of metal-containing material per one kg of a subject. In some embodiments, for a topical administration, the formulation can have a metal-containing material administered at a metal dosage of at least 0.1 mg of a metal-containing material (e.g., at least 0.4 mg, at least 40 mg, or at least 400 mg) and/or at most 10,000 mg (e.g., at most 5,000 mg, at most 1,000 mg, at most 400 mg, at most 40 mg, or at most 0.4 mg), and for a period sufficient to treat/alleviate/cure the condition. In some embodiments, the metal dosage is from 0.1 to 10,000 mg (e.g., from 0.1 to 5,000 mg, from 0.1 to 1,000 mg, from 0.4 to 1000 mg, from 0.4 to 400 mg, from 0.4 to 40 mg, from 40 to 400 mg) of metal-containing material. In some embodiments, for a 70 kg person, at least 20 mg (e.g., at least 50 mg, at least 100 mg, at least 200 mg, at least 300 mg, at least 400 mg, or at least 500 mg) and/or at most 600 mg (e.g., at most 500 mg, at most 400 mg, at most 300 mg, at most 200 mg, at most 100 mg, or at most 50 mg) of a metal-containing material is administered per single dose, or from 20 to 600 mg (e.g., from 50 to 500 mg, from 50 to 400 mg, from 20 to 400 mg, from 20 to 300 mg, from 20 to 200 mg) of a metal-containing material is administered per single dose.

The formulation can be administered to a subject (e.g., a human subject) at a dosage of at least one dose per day (e.g., at least one dose per 12 hours, or at least one dose per 6 hours) and/or at most one dose per three hours (e.g., at most one dose per six hours, or at most one dose per 12 hours). In some embodiments, the formulation is administered to a subject (e.g., a human subject) at a dosage of from one dose per day to one dose per three hours (e.g., from one dose per day to one dose per six hours, from one dose per day to one dose per 12 hours). The formulation can contact the area continuously, or for a duration of about one hour (e.g., about a half hour, about 15 minutes, about five minutes, about one minute).

Gastrointestinal Conditions

In some embodiments, for a gastrointestinal condition, the condition can be treated using by orally administering a formulation of metal-containing material, and/or by rectally administering a suppository and/or an enema including the metal-containing material. For example, the formulation can be a controlled-release composition (e.g., a tablet, pill, capsule, or bead having controlled-release properties and/or a controlled-release coating, an enteric-coated tablet, an enteric-coated pill, an enteric-coated capsule, a suspension including an enteric-coated bead), a nanodispersion, or a suppository having a metal-containing material administered at a metal dosage of at least 0.1 mg of a metal-containing material per one kg of a subject (e.g., at least 0.4 mg/kg, at least 40 mg/kg, or at least 400 mg/kg) and/or at most 1000 mg/kg (e.g., at most 400 mg/kg, at most 40 mg/kg, or at most 0.4 mg/kg), and for a period sufficient to treat/alleviate/cure the condition. In some embodiments, the metal dosage is from 0.1 to 10,000 mg (e.g., from 0.1 to 5,000 mg, from 0.1 to 1,000 mg, from 0.4 to 1000 mg, from 0.4 to 400 mg, from 0.4 to 40 mg, from 40 to 400 mg) of metal-containing material per one kg of a subject. In some embodiments, for a 70 kg person, at least 20 mg (e.g., at least 50 mg, at least 100 mg, at least 200 mg, at least 300 mg, at least 400 mg, or at least 500 mg) and/or at most 600 mg (e.g., at most 500 mg, at most 400 mg, at most 300 mg, at most 200 mg, at most 100 mg, or at most 50 mg) of a metal-containing material is administered per single dose, or from 20 to 600 mg (e.g., from 50 to 500 mg, from 50 to 400 mg, from 20 to 400 mg, from 20 to 300 mg, from 20 to 200 mg) of a metal-containing material is administered per single dose. In some embodiments, the formulation can take the form of an enema having a volume of about 60 ml (about 30 ml, about 40 ml, about 50 ml, about 70 ml, about 80 ml, or about 90 ml). The formulation can be administered to a subject at a dosage of at least one dose per day (e.g., at least one dose per 12 hours, or at least one dose per 6 hours) and/or at most one dose per three hours (e.g., at most one dose per six hours, or at most one dose per 12 hours). In some embodiments, the formulation is administered to a subject (e.g., a human subject) at a dosage of from one dose per day to one dose per three hours (e.g., from one dose per day to one dose per six hours, from one dose per day to one dose per 12 hours).

Examples of gastrointestinal conditions can include IBD, CDAD, ulcerative colitis, diarrhea, and botulism.

Circulatory and/or Systemic Conditions

In some embodiments, for a circulatory and/or a systemic condition, the condition can be treated by injecting (e.g., via a small needle injector, via an intravenous needle) a nanodispersion and/or a solution containing the metal-containing material into the subject. As another example, certain circulatory and/or systemic conditions can be treated by injecting (e.g., via a needleless injector) a powder (e.g., a freeze-dried powder, a free standing powder) of the metal-containing material into the subject. As a further example, certain circulatory and/or systemic conditions can be treated by orally administering a metal-containing material. In some embodiments, treatment includes a dosage of at least one dose per week (e.g., at least one dose per day, at least one dose per 12 hours, at least one dose per six hours, or at least one dose per three hours) and/or at most one dose per hour (e.g., at most one dose per three hours, at most one dose per six hours, or at most one dose per 12 hours). In some embodiments, the formulation is administered to a subject (e.g., a human subject) at a dosage of from one dose per day to one dose per three hours (e.g., from one dose per day to one dose per six hours, from one dose per day to one dose per 12 hours). In some embodiments, a dose includes a metal dosage of at least 0.1 milligram (mg) of a metal-containing material per kilogram (kg) of a subject (e.g., at least 0.5 mg/kg, at least one mg/kg, at least five mg/kg, at least 10 mg/kg, at least 50 mg/kg, at least 100 mg/kg, or at least 500 mg/kg) and/or at most 10,000 mg/kg (e.g., at most 5,000 mg, at most 1,000 mg, at most 500 mg/kg, at least 100 mg/kg, at most 50 mg/kg, at most 10 mg/kg, at most five mg/kg, at most one mg/kg, or at most 0.5 mg/kg). In some embodiments, a dose includes a metal dosage of from 0.1 mg to 10,000 mg (e.g., from 0.1 to 5,000 mg, from 0.1 to 1,000 mg, from 0.1 mg to 500 mg, from one mg to 500 mg, from 10 mg to 500 mg, from 50 mg to 500 mg, from 100 mg to 300 mg, from 100 mg to 200 mg) of a metal-containing material per kilogram (kg) of a subject. Areas of the circulatory system include, for example, the heart, the lymphatic system, blood, blood vessels (e.g., arteries, veins).

In certain embodiments, the circulatory and/or systemic condition is a bacterial and/or bacterial spore circulatory condition, a biofilm circulatory condition, a microbial circulatory condition, an inflammatory circulatory condition, an autoimmune circulatory condition, and/or an idiopathic circulatory condition. As referred to herein, circulatory conditions include lymphatic conditions. Examples of circulatory and/or systemic conditions include gas gangrene, tetanus, septicemia, leukemia, and lymphangitis.

Respiratory Conditions

In general, the treatment of respiratory conditions involves contacting the metal-containing material with the area of the respiratory system having the condition. Areas of the respiratory system include, for example, the oral cavity, the nasal cavity, and the lungs. As an example, certain respiratory conditions can be treated by inhaling a free standing powder and/or a freeze-dried powder of the metal-containing material (e.g., with a dry powder inhaler). As another example, certain respiratory conditions can be treated by inhaling a nanodispersion and/or solution containing the metal-containing material (e.g., in the form of an aerosol with an inhaler). The nanodispersion and/or solution can have a near-neutral pH. In some embodiments, when the nanodispersion and/or solution is in the form of an aerosol, the aerosol includes droplets having a diameter from 0.1 to 10 µm (e.g., from 0.1 to one µm, from one to five µm, or from five to 10 µm). The droplet size of an aerosol can determine how far down the respiratory tree the droplet travels. For example, a 10 µm droplet can pass the larynx and penetrate the trachea and bronchial regions of a lung, and settle at the pulmonary bifurcations. Droplets having a diameter of 0.1 to 2.5 µm can enter the nonciliated alveolar regions and deposit deep into the lungs of a subject.

In some embodiments, treatment includes a dosage of at least one dose per day (e.g., at least one dose per 12 hours, at least one dose per six hours, or at least one dose per three hours) and/or at most one dose per hour (e.g., at most one dose per three hours, at most one dose per six hours, or at most one dose per 12 hours). In some embodiments, the formulation is administered to a subject (e.g., a human subject) at a dosage of from one dose per day to one dose per three hours (e.g., from one dose per day to one dose per six hours, from one dose per day to one dose per 12 hours). In some embodiments, a dose includes a metal dosage of at least 0.1 milligram (mg) of a metal-containing material per kilogram (kg) of a subject (e.g., at least 0.5 mg/kg, at least one mg/kg, at least five mg/kg, at least 10 mg/kg, at least 50 mg/kg, at least 100 mg/kg, or at least 500 mg/kg) and/or at most 1000 mg/kg (e.g., at most 500 mg/kg, at most 100 mg/kg, at most 50 mg/kg, at most 10 mg/kg, at most five mg/kg, at most one mg/kg, or at most 0.5 mg/kg). In some embodiments, a dose includes a metal dosage of from 0.1 mg to 10,000 mg (e.g., from 0.1 to 5,000 mg, from 0.1 to 1,000 mg, from 0.1 mg to 500 mg, from one mg to 500 mg, from 10 mg to 500 mg, from 50 mg to 500 mg, from 100 mg to 300 mg, from 100 mg to 200 mg) of a metal-containing material per kilogram (kg) of a subject.

The respiratory condition can be a bacterial and/or bacterial spore respiratory condition, a biofilm respiratory condition, a microbial respiratory condition, an inflammatory respiratory condition, an autoimmune respiratory condition, and/or an idiopathic respiratory condition. Examples of respiratory conditions include anthrax infection, bronchitis, pulmonary edema, acute respiratory distress syndrome, bronchopulmonary dysplasia, fibrotic conditions (e.g., pulmonary fibrosis), tuberculosis, pneumonia, sinusitis, allergic rhinitis, pharyngitis, mucositis, stomatitis, chronic obstructive pulmonary disease, bronchiectasis, lupus pneumonitis, and/or cystic fibrosis.

Skin or Integument Conditions

Generally, the treatment of skin or integument conditions involves contacting the metal-containing material with the area of the skin having the condition. As an example, a skin or integument condition can be treated by contacting the area of skin having the condition with a dressing having a coating of the metal-containing material. As another example, a skin or integument condition can be treated by contacting the area of skin having the condition with a nanodispersion/solution containing the metal-containing material. As an additional example, a skin or integument condition can be treated by contacting the area of skin having the condition with a pharmaceutical carrier composition containing the metal-containing material, such as a cream, a foam, a gel, a lotion, a paste, an ointment, a nanodispersion and/or a solution. Treatment can continue until the condition is cured or ameliorated. In some embodiments, when the condition is anthrax, gas gangrene, or tetanus, the material may be applied to the affected skin area in the form of foam, gel, lotion, paste, and/or ointment at a concentration of from 100 µg to 20000 µg metal-containing material per gram of the formulation; or nanodispersion and/or solution that can include the metal-containing material at a concentration of from 100 µg to 20000 µg per ml of the formulation. In some embodiments, the nanodispersion and/or solution can include from one µg to 100 µg (e.g., from one µg to 50 µg, from one µg to 25 µg, from 50 µg to 100 µg) metal-containing material per ml of the formulation. A topical administration can kill the spores and bacteria at an area of skin such that the infection does not become systemic. In some embodiments, the formulation can include liposomes, micelles, or vesicles intended to improve the penetration of the silver through epidermal and dermal tissue.

In some embodiments, treatment includes a dosage of at least one dose per day (e.g., at least one dose per 12 hours, at least one dose per six hours, or at least one dose per three hours) and/or at most one dose per hour (e.g., at most one dose per three hours, at most one dose per six hours, or at most one dose per 12 hours). In some embodiments, the formulation is administered to a subject (e.g., a human subject) at a dosage of from one dose per day to one dose per three hours (e.g., from one dose per day to one dose per six hours, from one dose per day to one dose per 12 hours). In some embodiments, a dose includes at least 0.2 gram (e.g., at least 0.4 gram, at least 0.6 gram, at least 0.8 gram, at least one gram, at least two grams, at least three grams, or at least four grams) and/or at most five grams (e.g., at most four grams, at most three grams, at most two grams, at most one gram, at most 0.8 gram, at most 0.6 gram, or at most 0.4 gram) of a formulation per area of about 200 cm$^2$ (e.g., about 150 cm$^2$, about 100 cm$^2$, about 80 cm$^2$, about 60 cm$^2$, about 40 cm$^2$, about 20 cm$^2$, or about 10 cm$^2$). In some embodiments, a dose includes from 0.2 gram to five grams (e.g., from 0.4 to four grams, from 0.3 to three grams, from one to four grams, from one to three grams, from one to two grams) of a formulation per area of about 200 cm$^2$ (e.g., about 150 cm$^2$, about 100 cm$^2$, about 80 cm$^2$, about 60 cm$^2$, about 40 cm$^2$, about 20 cm$^2$, or about 10 cm$^2$).

The skin condition or an integument condition can be a bacterial and/or bacterial spore skin condition, a biofilm skin condition, an inflammatory skin condition, an autoimmune skin condition, an idiopathic skin condition, a microbial integument condition, an inflammatory integument condition, an autoimmune integument condition, and/or an idiopathic integument condition. Examples of skin conditions or integument conditions include burns, pyoderma gangrenosum, erythema multiforme, rosacea, acne (e.g., acne vulgaris, neonatal acne, infantile acne, pomade acne), Reiter's syndrome, gas gangrene, tetanus, anthrax, ulcer and erosion due to cutaneous trauma (e.g., diabetic foot ulcer).

Formulations

Controlled-Release Compositions

In some embodiments, the formulation is a controlled-release composition. The controlled-release formulation can be designed to selectively release a therapeutic agent in a desired area of the small and/or large intestines, and/or gradually release the therapeutic agent over a selected area of the small and/or large intestines. The controlled-release composition can include articles (e.g., beads, tablets, pills, capsules) including a therapeutic agent (e.g., one or more metal-containing materials and/or one or more non-metal antibiotic medications). The articles can be coated with a controlled-release coating. The controlled-release coating provides a protective barrier for the therapeutic agent against acidic environments (e.g., the stomach) so that the formulation passes through the stomach with little (e.g., no) therapeutic agent being released, and so that the therapeutic agent is relatively easily released in less acidic environments (e.g., the intestines, the colon). In some embodiments, the controlled-release coating can control the release the therapeutic agent in a desired area of the small and/or large intestines, and/or gradually release the therapeutic agent over a selected area of the small and/or large intestines.

In some embodiments, the controlled-release composition includes a controlled-release bead (e.g., a bead having controlled-release properties and/or a controlled-release coating, an enteric-coated bead). In general, the bead can have a variety of cross-sectional shapes, such as a circle, an ellipse, a regular polygon (e.g., a square, a diamond, a pentagon, a hexagon, or an octagon), and/or an irregular polygon. For example, in some embodiments, the bead is a sphere and has a circular cross-section. The bead can have a maximum average dimension (e.g., a diameter) of from 0.1 to three mm (e.g., from 0.5 to two mm, from 0.5 to one mm, or from one to two mm). In some embodiments, the bead can have a maximum average dimension of at least 0.1 mm (e.g., at least 0.5 mm, at least one mm, at least 1.5 mm, at least two mm) and/or at most three mm (e.g., at most two mm, at most 1.5 mm, at most one mm, or at most 0.5 mm). The maximum average dimension of a bead is determined by measuring the maximum dimension of each bead in a population of beads (e.g., 10, 20, or 50 beads), adding the maximum dimension of each bead, and dividing the sum by the number of measured beads.

In some embodiments, the controlled-release bead has a core that includes a biocompatible and/or bioabsorbable material such as a carbohydrate (e.g., sugar, starch, sodium carboxymethylcellulose, cellulose, alginates, and/or sodium starch glycolate).

In some embodiments, the core is coated with a therapeutic agent, such as a metal-containing material and/or an non-metal antibiotic medication. In some embodiments, the therapeutic agent is uniformly or non-uniformly distributed throughout the core. For example, the therapeutic agent remain at a constant concentration, or can increase or decrease in concentration from the periphery of the bead to the center of the core. The controlled-release bead can include from 0.01 to 20 percent by weight (e.g., from 0.05 to 20 percent, from one to 20 percent, from 0.05 to 10 percent, or from 0.05 to five percent) of the therapeutic agent (e.g., a metal-containing material and/or an non-metal antibiotic medication). In some embodiments, the controlled-release bead can include at least 0.01 percent by weight (e.g., at least 0.05 percent by weight, at least 0.1 percent by weight, at least 0.5 percent by weight, at least one percent by weight, at least five percent by weight, at least 10 percent by weight, or at least 15 percent by weight) and/or at most 20 percent by weight (at most 15 percent by weight, at most 10 percent by weight, at most five percent by weight, at most one percent by weight, at most 0.5 percent by weight, at most 0.1 percent by weight, or at most 0.05 percent by weight) of the therapeutic agent.

The controlled-release bead can have a surface covered with a controlled-release coating (e.g., an enteric coating). The coating can include a material that is stable in acidic environments, but that disintegrates relatively rapidly in less acidic environment. Examples of controlled-release coatings include beeswax, beeswax and glyceryl monostearate, shellac and cellulose, cetyl alcohol, mastic and shellac, shellac and stearic acid, polyvinyl acetate and ethyl cellulose, neutral copolymer of polymethacrylic acid ester (Eudragit L30D), copolymer of methacrylic acid and methacrylic acid methylester (Eudragits), neutral copolymers of polymethacrylic acid esters containing metallic stearates, neutralized hydroxypropyl methylcellulose phthalate polymer, and/or combinations thereof.

In some embodiments, the controlled-release composition can include more than one type of controlled-release beads, each type having any combination of therapeutic agent, maximum average dimension, concentration, distribution of therapeutic agent, core materials, and/or coating materials.

In some embodiments, the controlled-release beads are made by forming a granulated wet mixture of core materials (e.g., a carbohydrate), a binder and/or a therapeutic agent, extruding the mixture, and forming beads by placing the extrudate into a spheronizer. In some embodiments, a bead having a core without any therapeutic agents can be sprayed with a solution and/or a dispersion (e.g., a nanodispersion) of a therapeutic agent. The weight percent of the therapeutic agent can be determined by measuring the bead before and after coating, or by pre-measuring the mass of each component of a bead prior to forming a mixture of core materials. Methods for making coated compositions are described, for example, in Garcia et al., U.S. Pat. No. 7,217,429, and Ullah et al., U.S. Pat. No. 6,224,910. In some embodiments, the bead core are commercially available (e.g., from Chr. Hansen, Denmark).

In some embodiments, the controlled-release beads are pressed into a tablet or a pill, encapsulated in a capsule, or suspended in a solution to form a suspension. In some embodiments, a tablet, pill, or capsule can be formed directly from a therapeutic agent and any of a number of excipients, binders, and/or fillers. The tablet, pill, or capsule can contain varying percentage amounts of the therapeutic agents and carriers. For example, the tablet, pill, or capsule can contain more than 0.01 percent (e.g., more than 0.1 percent, more than one percent, more than five percent, or more than 10 percent) and/or less than 20 percent by weight (e.g., less than 10 percent, less than five percent, less than one percent, or less than 0.1 percent) of the therapeutic agent (e.g., a metal-containing material and/or a non-metal antibiotic medication). Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The tablet, pill, or capsule can then be coated with a controlled-release coating.

In some embodiments, to deliver the controlled-release composition to an area of a subject, the composition can be ingested by a subject, injected into a subject, or delivered as a suppository or enema to a subject. Examples of formulations and methods for delivery of medicaments to the intestinal tract for increased absorption are described, for example, in Davis, Drug Discovery Today, 10(4) 2005, 249-257; Fell, J. Anat. (1996) 189, 517-519; Ibekwe et al., The Drug Discovery Companies Report Spring/Summer 2004 (2004) 27-30.

Creams

In some embodiments, the formulation is a cream that has a cosmetically acceptable appearance, such as a uniform color and texture, and be absent of offensive odors. The metal-containing material can be dispersed (e.g., uniformly distributed) within a cream. The metal-containing material can be in the form of particles having a maximum dimension of at most five microns (e.g., at most four microns, at most three microns, at most two microns, at most one micron, at most 500 nm, at most 400 nm, at most 300 nm, at most 200 nm, or at most 100 nm). In some embodiments, the particles are agglomerated, and can form clusters of agglomerated particles having a maximum dimension of at most 25 microns (e.g., at most 20 microns, at most 15 microns, or at most 10 microns).

The cream can include components such as: water, cetearyl alcohol, glycerol monostearate, stearic acid, light mineral oil, isopropyl myristate, polyoxyl 40 stearate, propylparaben, methylparaben, xanthan gum (e.g., Xantural), white petrolatum, polyethylene glycol (e.g., PEG 400, PEG 300), titanium dioxide, propylene glycol, diethylene glycol monoethyl ether (Transcutol), cetyl alcohol, benzyl alcohol, hexylene glycol, EDTA, (hydroxypropyl)methylcellulose (HPMC), sodium benzoate, hydroxypropylcellulose (HPC), methyl cellulose (e.g., methyl cellulose A4M), sodium carboxymethylcellulose, sodium parabens, crosslinked polyacrylate polymer (e.g., Carbopol), and/or carrageenan.

In some embodiments, the cream includes at least 0.1 percent (e.g., at least 0.2 percent, at least 0.3 percent, at least 0.4 percent, at least 0.5 percent, at least 0.6 percent, at least 0.8 percent, at least one percent, at least 1.5 percent, at least two percent, at least three percent, or at least four percent) and/or at most five percent (at most four percent, at most three percent, at most two percent, at most 1.5 percent, at most one percent, at most 0.8 percent, at most 0.6 percent, at most 0.5 percent, at most 0.4 percent, at most 0.3 percent, or at most 0.2 percent) by weight of a metal-containing material. In some embodiments, the cream includes from 0.1 to five (e.g., from 0.1 to two, from 0.1 to one, from 0.1 to 0.5, from 0.2 to four, from 0.4 to three, from 1 to three, from two to three) percent by weight of a metal-containing material. In some embodiments, the cream includes from 100 µg to 20000 µg (e.g., from 100 µg to 10000 µg, from 100 µg to 1000 µg, from 1000 µg to 20000, or from 1000 to 20000 µg) of the metal-containing material per gram of the cream. In some embodiments, the concentration of the metal-containing material in a cream is at most the minimum inhibitory concentration for a given bacterium species (e.g., a sporulating bacterium species).

In some embodiments, the cream includes at least one percent (e.g., at least 1.5 percent at least two percent, at least three percent, at least 3.5 percent, at least four percent, at least five percent, at least six percent, at least seven percent, at least eight percent, or at least nine percent) and/or at most ten percent (e.g., at most nine percent, at most eight percent, at most seven percent, at most six percent, at most five percent, at most four percent, at most 3.5 percent, at most three percent, at most two percent, or at most 1.5 percent) by weight of white petrolatum. In some embodiments, the cream includes from one to ten (e.g., from one to eight, from 1.5 to 3.5, from two to seven, from three to seven, from four to seven, from four to six) percent by weight of white petrolatum. White petrolatum is an emollient, and can moisturize an area of the skin by decreasing evaporation from the skin.

In some embodiments, the cream includes at least one percent (e.g., at least two percent, at least three percent, at least four percent, at least five percent, at least six percent, at least seven percent, at least eight percent, or at least nine percent) and/or at most ten percent (e.g., at most nine percent, at most eight percent, at most seven percent, at most six percent, at most five percent, at most four percent, at most three percent, or at most two percent) by weight of isopropyl myristate. In some embodiments, the cream includes from one to ten (e.g., from two to nine, from three to eight, from three to ten, from 3.5 to 4.5, from four to seven, from four to six) percent by weight of isopropyl myristate. Isopropyl myristate can be a moisturizing agent and an emollient, and can be unreactive with the metal-containing material. In some embodiments, isopropyl myristate is a vehicle for the metal-containing material and can enhance the absorption of the metal-containing material through the skin.

In some embodiments, the cream includes at least 0.5 percent (e.g., at least one percent, at least two percent, at least three percent, at least 3.5 percent, or at least four percent) and/or at most five percent (e.g., at most four percent, at most 3.5 percent, at most three percent, at most two percent, or at most one percent) by weight of polyoxyl 40 stearate. In some embodiments, the cream includes from 0.5 to five (e.g., from one to five, from one to four, from one to three, from one to two, from two to five, from two to four) percent by weight of polyoxyl 40 stearate. Polyoxyl 40 stearate is a nonionic surface-active agent, and can be an emulsifying agent in a cream.

In some embodiments, the cream includes at least two percent (e.g., at least three percent, at least four percent, at least five percent, at least six percent, at least seven percent, at least eight percent, or at least nine percent) and/or at most ten percent (e.g., at most nine percent, at most eight percent, at most seven percent, at most six percent, at most five percent, at most four percent, or at most three percent) by weight of cetearyl alcohol. In some embodiments, the cream includes from two to ten (e.g., from two to nine, from three to eight, from three to ten, from four to seven, from four to six) percent by weight of cetearyl alcohol. Cetearyl alcohol can form an occlusive film and decrease the likelihood of skin moisture evaporation.

In some embodiments, the cream includes at least one percent (e.g., at least two percent, at least three percent, at least 3.5 percent, or at least four percent) and/or at most five percent (e.g., at most four percent, at most 3.5 percent, at most three percent, or at most two percent) by weight of cetyl alcohol. In some embodiments, the cream includes from one to five (e.g., from one to four, from one to three, from two to five, from two to four, from three to five, from 3.5 to 4.5, from four to five) percent by weight of cetyl alcohol. In some embodiments, cetyl alcohol is an emollient, a thickening agent, and/or can lighten the color of the cream (e.g., a cream including a metal-containing material).

In some embodiments, the cream includes at least one percent (e.g., at least two percent, at least three percent, at least 3.5 percent, or at least four percent) and/or at most five percent (e.g., at most four percent, at most 3.5 percent, at most three percent, or at most two percent) by weight of glycerol monostearate. In some embodiments, the cream includes from one to five (e.g., from one to four, from one to three, from two to five, from two to four, from three to five, from four to five) percent by weight of glycerol monostearate. Glycerol monostearate can provide moisturizing properties and/or can thicken the cream.

In some embodiments, the cream includes at least one percent (e.g., at least two percent, at least three percent, at least 3.5 percent, at least four percent, at least five percent, at least six percent, at least seven percent, at least eight percent, at least nine percent, at least ten percent, at least 12 percent, at least 15 percent, or at least 17 percent) and/or at most 20 percent (e.g., at most 17 percent, at most 15 percent, at most 12 percent, at most ten percent, at most nine percent, at most eight percent, at most eight percent, at most seven percent, at most six percent, at most five percent, at most four percent, at most 3.5 percent, at most three percent, or at most two percent) by weight of stearic acid. In some embodiments, the cream can include from one to 20 (e.g., from one to 15, from one to 10, from two to ten, from two to eight, from two to seven, from three to eight, from three to six, from four to six) percent by weight of stearic acid. Addition of stearic acid can result in a lighter-colored cream, and can decrease the likelihood of discoloration. In some embodiments, stearic acid can stabilize the cream and can help maintain the cream in a similar color and texture for a period of time (e.g., at least one month, at least two months, at least three months, at least six months, or at least a year) after cream formation. In some embodiments, stearic acid is an emollient and can provide moisturizing properties to skin.

In some embodiments, the cream includes at least one percent (e.g., at least two percent, at least three percent, at least four percent, at least five percent, at least six percent, at least seven percent, at least eight percent, or at least nine percent) and/or at most ten percent (e.g., at most nine percent, at most eight percent, at most seven percent, at most six percent, at most five percent, at most four percent, at most three percent, or at most two percent) by weight of a poly (ethylene glycol). In some embodiments, the cream includes from one to ten (e.g., from two to nine, from three to eight, from three to ten, from four to seven, from four to six, from five to seven, from 5.5 to 6.5) percent by weight of polyethylene glycol. An example of a polyethylene glycol is PEG 400. PEG 400 can be compatible with a metal-containing material and enhance the texture of the cream to produce a smooth feeling during application. In some embodiments, PEG 400 can stabilize the cream. In some embodiments, PEG 400 can slow the drying process of the formulation and moisturize a skin area to which the cream has been applied.

In some embodiments, the cream includes at least 0.1 percent (e.g., at least 0.2 percent, at least 0.3 percent, at least 0.4 percent, at least 0.5 percent, at least 0.6 percent, at least 0.7 percent, at least 0.8 percent, at least one percent, at least two percent, at least three percent, or at least four percent) and/or at most five percent (e.g., at most four percent, at most three percent, at most two percent, at most one percent, at most 0.8 percent, at most 0.7 percent, at most 0.6 percent, at most 0.5 percent, at most 0.4 percent, at most 0.3 percent, or at most 0.2 percent) by weight of benzyl alcohol. In some embodiments, the cream includes from 0.1 to seven (e.g., from 0.1 to five, from 0.1 to two, from 0.1 to one, from 0.1 to 0.5, from 0.2 to four, from 0.4 to three, from one to two, from 1 to three, from two to three) percent by weight of benzyl alcohol. In some embodiments, benzyl alcohol is a preservative and can decrease the likelihood of microbial proliferation in the cream. In some embodiments, benzyl alcohol is absent when the cream includes a metal-containing material.

In some embodiments, the cream includes at least one percent (e.g., at least two percent, at least three percent, at least four percent, at least five percent, at least six percent, at least seven percent, at least eight percent, or at least nine percent) and/or at most 10 percent (e.g., at most nine percent, at most eight percent, at most seven percent, at most six percent, at most five percent, at most four percent, at most three percent, at most two percent, or at most one percent) by weight of titanium dioxide. In some embodiments, the cream includes from one to ten (e.g., from two to nine, from three to eight, from three to ten, from four to seven, from four to six, from five to seven, from 5.5 to 6.5) percent by weight of titanium dioxide. Titanium dioxide can lighten the color of the cream, for example, to provide a more aesthetically pleasing color. In some embodiments, titanium dioxide is coated with stearic acid prior to addition to a cream. In certain embodiments, titanium dioxide is coated with stearic acid in situ during formation of the cream. In some embodiments, titanium dioxide is not coated with stearic acid prior to addition to a formulation, or during formation of the cream.

In some embodiments, the cream includes at least two percent (e.g., at least three percent, at least four percent, at least five percent, at least six percent, at least seven percent, at least eight percent, or at least nine percent) and/or at most ten percent (e.g., at most nine percent, at most eight percent, at most seven percent, at most six percent, at most five percent, at most four percent, or at most three percent) by weight of light mineral oil. In some embodiments, the cream includes from two to ten (e.g., from two to nine, from three to eight, from three to ten, from four to seven, from four to six, from five to seven) percent by weight of light mineral oil. Light mineral oil is an emollient and can moisturize the skin to which the cream is applied.

In certain embodiments, the cream can include at least 0.01 percent (e.g., at least 0.02 percent, at least 0.03 percent, at least 0.05 percent, at least 0.1 percent, at least 0.2 percent, at least 0.3 percent, or at least 0.4 percent) and/or at most 0.5 percent (e.g., at most 0.4 percent, at most 0.3 percent, at most 0.2 percent, at most 0.1 percent, at most 0.05 percent, or at most 0.03 percent) by weight of propyl paraben. In some embodiments, the cream can include from 0.01 to 0.5 (e.g., from 0.01 to 0.3, from 0.02 to 0.4, from 0.01 to 0.05, from 0.1 to 0.3) percent by weight of propyl paraben. Propyl paraben can be a preservative and decrease the likelihood of microbial proliferation in the cream. In some embodiments, propyl paraben is absent when the cream contains a metal-containing material.

In certain embodiments, the cream can include at least 0.05 percent (e.g., at most 0.1 percent, at most 0.15 percent, at most 0.2 percent, at most 0.3 percent, or at most 0.4 percent) and/or at most 0.5 percent (e.g., at most 0.4 percent, at most 0.3 percent, at most 0.2 percent, at most 0.15 percent, or at most 0.1 percent) by weight of methyl paraben. In some embodiments, the cream includes from 0.05 to 0.5 (e.g., from 0.1 to 0.4, from 0.2 to 0.3) percent by weight of methyl paraben. Methyl paraben can be a preservative and decrease the likelihood of microbial proliferation in the cream. In some embodiments, methyl paraben is absent when the cream contains a metal-containing material.

In certain embodiments, the cream can include at least 0.02 percent (e.g., at least 0.05 percent, at least 0.1 percent, at least 0.2 percent, at least 0.3 percent, or at least 0.4 percent) and/or at most 0.5 percent (e.g., at most 0.4 percent, at most 0.3 percent, at most 0.2 percent, at most 0.1 percent, or at most 0.05 percent) by weight of xanthan gum. In some embodiments, the cream includes from 0.02 to 0.5 (e.g., from 0.1 to 0.4, from 0.2 to 0.3) percent by weight of xanthan gum. Xanthan gum can help thicken a formulation and help suspend the components of the cream to form a homogeneous mixture. In some embodiments, xantham gum is absent when the cream contains a metal-containing material.

In some embodiments, the cream can include at least 20 percent (e.g., at least 30 percent, at least 50 percent, at least 70 percent, at least 80 percent, or at least 90 percent) and/or at most 99 percent (e.g., at most 90 percent, at most 80 percent, at most 70 percent, at most 50 percent, or at most 30 percent) by weight water.

In some embodiments, the cream can include at least zero percent (e.g., at least 0.1 percent, at least 0.3 percent, at least 0.5 percent, at least 0.7 percent, at least 0.9 percent, at least one percent, at least 1.2 percent, at least 1.4 percent, at least 1.6 percent, or at least 1.8 percent) and/or at most two percent (e.g., at most 1.8 percent, at most 1.6 percent, at most 1.4 percent, at most 1.2 percent, at most 0.9 percent, at most 0.7 percent, at most 0.5 percent, at most 0.3 percent, or at most 0.1 percent) by weight of iron oxide. In some embodiments, the cream includes from 0 to two (e.g., from 0.5 to one, from 0.3 to 0.5, from 0.3 to one) percent by weight iron oxide. Iron oxide can be added for color matching between creams having different concentrations of a metal-containing material.

Nanodispersions

In some embodiments, the material can be in the form of a nanodispersion. A nanodispersion refers to a suspension of one or more metal-containing materials including small particles having a maximum dimension of about 400 nm or less (e.g., about 300 nm or less, about 200 nm or less, about 150 nm or less, about 100 nm or less, about 50 nm or less, or about 25 nm or less) and/or at least 10 nm (e.g., at least 25 nm, at least 50 nm, at least 100 nm, at least 150 nm, at least 200 nm, or at least 300 nm). In some embodiments, the particles have a maximum dimension of from 10 to 400 (e.g., from 10 to 200, from 10 to 75, from 10 to 50, from 10 to 40) nanometers. In some embodiments, in addition to small particles, the nanodispersion can further include large particles having a maximum dimension of 400 nm or more (e.g., 300 nm or more, 200 nm or more, 150 nm or more, about 100 nm or more, about 50 nm or more, about 25 nm or more). The small particles can be released from micron-sized particles and/or from the large particles, for example, by ultrasonication. A nanodispersion can a be a stable or unstable system of particles evenly distributed in a solvent. The nanodispersion can be substantially more therapeutically effective (e.g., 2× more effect, 5× more effective, 10× more effective, 20× more effective, 50× more effective, 100× more effective) than a suspension of metal-containing materials that does not contain small particles, such that a smaller quantity of metal-containing material (e.g., 1/100 of a quantity, 1/50 of a quantity, 1/20 of a quantity, 1/10 of a quantity, 1/5 of a quantity, 1/2 of a quantity) is needed in a nanodispersion to achieve the same therapeutic effect as a suspension that does not contain small particles. A decreased quantity of a metal-containing material in a formulation can have decreased toxicological effect on a subject, and can facilitate the administration of a formulation.

Without wishing to be bound by theory, it is believed that the particles within a nanodispersion can contain a mixture of metal-containing material in various proportions. For example, in some embodiments, the metal-containing material in a nanodispersion includes less than 70% (e.g., less than 60%, less than 50%, less than 40%, less than 30%) and/or more than 25% (e.g., more than 30%, more than 40%, more than 50%, or more than 60%) by weight Ag(0); less than 70% (e.g., less than 65%, less than 55%, less than 45%, or less than 35%) and/or more than 30% (e.g., more than 35%, e.g., more than 45%, more than 55%, or more than 65%) by weight $Ag_2O$; and/or less than 10% (e.g., less than 7%, less than 5%, or less than 3%) and/or more than 1% (e.g., more than 3%, more than 5%, or more than 7%) $Ag_2CO_3$.

The nanodispersion can be formed, for example, by dispersing a free standing powder of the material in a solution and sonicating the mixture. In some embodiments, the nanodispersion is formed by stirring a free standing powder of the material while heating to an elevated temperature (e.g., from about 50° C. to about 90° C., from about 60° C. to about 80° C., from about 60° C. to about 70° C., or about 60° C.) for a period of time (e.g., from about 20 minutes to one hour, from about 20 to about 40 minutes, or from about 20 to 30 minutes). In some embodiments, a container (e.g., a tea bag-type container) with the free standing powder within it can be immersed in the water or solvent to disperse the free standing powder, the mixture can then be sonicated using an ultrasonicator (e.g., a probe sonicator such as Hielscher UP400S and/or Sonifier Model #250). In some embodiments, a substrate (e.g., in the form of a strip or a bandage) carrying the material can be immersed in the solvent to disperse the metal-containing material. The solvent containing the substrate can be shaken in a shaking incubator (e.g., at 180 RPM and 37° C. for 30 minutes) and/or stirred, and the mixture can then be sonicated. In some embodiments, formation of the nanodispersion further includes separating a supernatant nanodispersion from a precipitate, for example, by decantation and/or by filtration.

The nanodispersion solvent can be an aqueous or an organic solvent. For example, the solvent can be an alcohol (e.g., propanol, ethanol), an organic solvent (e.g., DMSO, azone), or water. The aqueous solvent can be a solution or a buffer, such as a lactate buffer, an EDTA buffer, a citrate buffer, a glycolate buffer, or a gluconate buffer. The buffer can have a pH at least 3 (e.g., at least 4, at least 5, at least 6, at least 7, or at least 8) and/or at most 9 (e.g., at most 8, at most 7, at most 6, at most 5, or at most 4). In some embodiments, the buffer has a pH of from 3 to 9 (e.g., from 4 to 8, from 3 to 7, from 4 to 6, from 5 to 7). The buffer concentration can be at least 0.05 M (e.g., at least 0.1 M, at least 0.2 M, at least 0.3 M, or at least 0.4 M) and/or at most one M (e.g., at most 0.5M, at most 0.4 M, at most 0.3 M, at most 0.2 M, or at most 0.1 M). In some embodiments, the buffer concentration can be from 0.05 to one M (e.g., from 0.1 to one M, from 0.2 to 0.5 M, from 0.3 to 0.5 M).

The nanodispersion can include a stabilizing agent, such as surfactant and/or an emulsifier. A stabilizing agent stabilizes nanodispersions by decreasing the likelihood of agglomeration of individual particles. Examples of stabilizing agents include surfactants and/or emulsifiers, such as docusate sodium, sodium lauryl sulfate, cetrimide, PEG povidone, propylene glycol, propylene glycol alginate, benzalkonium chloride, poloxamer, polyethylene alkyl ethers, sorbitan esters, xanthan gum, polysorbate (e.g., Tween 80), lecithin, pectin, polysorbate, sorbitan (e.g., SPAN) and/or polyvinyl alcohol (PVA). In some embodiments, a stabilizing agent helps suspend the metal-containing material and provides a homogeneous nanodispersion. In some embodiments, a stabilizing agent lowers the surface charge of the particles and decreases the attraction between the particles. In some embodiments, a stabilizing agent (e.g., PVA) acts as a physical barrier between particles to decrease contact between the particles. In other embodiments, stabilizing agents (e.g., lecithin) change the charge on the particles to increase particle-particle repulsion. The surface charge on the particles is assessed by measuring the zeta potential using a Zetasizer nano-ZS instrument (Malvern Instruments Ltd).

The nanodispersion can include one or more surfactants/emulsifiers at a concentration of at least 0.1 percent by weight (e.g., at least 0.5 percent by weight, at least one percent by weight, at least two percent by weight, at least three percent by weight, at least four percent by weight, at least five percent by weight, at least six percent by weight, at least seven percent by weight, at least eight percent by weight, or at least nine percent by weight) and/or at most ten percent by weight (e.g., at most nine percent by weight, at most eight percent by weight, at most seven percent by weight, at most six percent by weight, at most five percent by weight, at most four percent by weight, at most three percent by weight, at most two percent by weight, at most one percent by weight, or at most 0.5 percent by weight). In some embodiments, the nanodispersion includes from 0.01 to ten (e.g., from 0.01 to eight, from 0.5 to eight, from 0.5 to six, from 0.5 to four, from 0.5 to two, from one to eight, from one to six, from one to two, from two to eight, from two to six, from two to three, from four to eight, from four to six) percent by weight of one or more surfactants/emulsifiers.

The nanodispersion can include one or more metal-containing materials at a concentration of at least 0.00001 percent by weight (e.g., at least 0.0001 percent by weight, at least 0.001 percent by weight, at least 0.01 percent by weight, at least 0.1 percent by weight, at least one percent by weight, at least two percent, at least three percent, or at least four percent) and/or at most five percent by weight (e.g., at most four percent, at most three percent, at most two percent, at most one percent by weight, at most 0.1 percent by weight, at most 0.01 percent by weight, at most 0.001 percent by weight, or at most 0.0001 percent by weight). In some embodiments, the nanodispersion includes from 0.00001 to five (e.g., from 0.0001 to five, from 0.001 to five, from 0.01 to five, from 0.1 to five, from one to five, from 0.0001 to three, from 0.001 to three, from 0.01 to three, from 0.1 to three, from one to three, from 0.0001 to one, from 0.001 to one, from 0.01 to one, from 0.1 to one, from 0.1 to 0.5) percent by weight of one or more metal-containing materials. In certain embodiments, the nanodispersion includes the metal-containing material at a concentration of at least 1 µg of metal-containing material per one ml nanodispersion (e.g., at least 5 µg/ml, at least 10 µg/ml, at least 20 µg/ml, at least 30 µg/ml, at least 40 µg/ml, at least 50 µg/ml, or at least 75 µg/ml) and/or at most 100 µg/ml (e.g., at most 75 µg/ml, at most 50 µg/ml, at most 40 µg/ml, at most 30 µg/ml, at most 20 µg/ml, at most 10 µg/ml, or at most 5 µg/ml). In certain embodiments, the nanodispersion includes from 1 to 100 (e.g., from 1 to 75, from 1 to 50, from 1 to 25, from 10 to 100, from 10 to 75, from 10 to 50, from 10 to 20) µg of metal-containing material per one ml nanodispersion. In some embodiments, the concentration of the metal-containing material in a nanodispersion is at most the minimum inhibitory concentration for a given bacterium species (e.g., a sporulating bacterium species).

In some embodiments, the nanodispersion can include at least 100 µg of metal-containing material per one ml of nanodispersion (e.g., at least 1,000 µg/ml, at least 5,000 µg/ml, at least 10,000 µg/ml, or at least 15,000 µg/ml) and/or at most 20,000 µg/ml (at most 15,000 µg/ml, at most 10,000 µg/ml, at most 5000 µg/ml, at most 1,000 µg/ml). For example, the nanodispersion can include from 100 µg to 20000 µg (e.g., from 100 to 10000 µg, from 100 µg to 1000 µg, from 1000 µg to 20000 µg, or from 1000 to 20000 µg) of the metal-containing material per one ml of nanodispersion.

In certain embodiments, the nanodispersion containing the material is contacted with the subject relatively soon after formation of the nanodispersion. For example, the nanodispersion containing the material can be contacted with the subject within about one minute or less (e.g., within about 30 seconds or less, within about 10 seconds or less) of forming the nanodispersion. In some embodiments, a longer period of time lapses before the nanodispersion containing the material is contacted with the subject. For example a period of time of at least about 1.5 minutes (e.g., at least about five minutes, at least about 10 minutes, at least about 30 minutes, at least about one hour, at least about 10 hours, at least about a day, or at least about a week) lapses between the time the solution containing the material is formed and the nanodispersion containing the material is contacted with the subject.

In some embodiments, the metal-containing material can be in the form of a foam, a spray, or a drop. The foam, spray, or drop can have the same composition as a nanodispersion.

Solutions

In some embodiments, the metal-containing material is in the form of a solution including dissolved metal species. The dissolved metal species can be ionic. The solution is relatively free of particulates having a size greater than one nm. The solution can be formed by dissolving a free standing powder of the material in a solvent for the powder, and filtering the mixture through a filter (e.g., a 0.1 micron filter, a 0.2 micron filter). As an example, a container (e.g., a tea bag-type container) with the free standing powder within it can be immersed in the water or solvent and the resulting solution can be filtered. As another example, a substrate (e.g., in the form of a strip or a bandage) carrying the material can be immersed in the solvent to disperse the metal-containing material. The solvent containing the substrate can be shaken in a shaking incubator (e.g., at 180 RPM and 37° C. for 30 minutes) and/or stirred, then filtered.

The solution includes a solvent that can be an aqueous or an organic solvent. For example, the solvent can be an alcohol (e.g., propanol, ethanol) or an organic solvent. As an example, the solvent can be carbonated water, which can be prepared by sparging $CO_2$ through water using, for example, a $CO_2$ Soda Syphon charger. The pH of the solution can be lowered by adding $CO_2$ to the solution to form carbonic acid. In some embodiments, the solvent is a buffer, such as a lactate buffer, an EDTA buffer, a citrate buffer, a glycolate buffer, a gluconate buffer. The buffer can have a pH at least 3 (e.g., at least 4, at least 5, at least 6, at least 7, or at least 8) and/or at most 9 (e.g., at most 8, at most 7, at most 6, at most 5, or at most 4). In some embodiments, the buffer has a pH of from 3 to 9 (e.g., from 4 to 8, from 3 to 7, from 4 to 6, from 5 to 7). The buffer concentration can be at least 0.05 M (e.g., at least 0.1 M, at least 0.2 M, at least 0.3 M, at least 0.4 M, at least 0.5 M, or at least 0.7M) and/or at most one M (e.g., at most 0.7 M, at most 0.5 M, at most 0.4 M, at most 0.3 M, at most 0.2 M, or at most 0.1 M). In some embodiments, lowering the pH of the solution (e.g., to less than about 6.5, such as from about 3.5 to about 6.5) can allow for a higher concentration of the dissolved material and/or a faster rate of dissolution.

In some embodiments, the solution contains at least 0.00001 percent by weight (e.g., greater than 0.0001 percent by weight, at least 0.001 percent by weight, at least 0.01 percent by weight, at least 0.1 percent by weight, at least one percent by weight, at least two percent by weight, at least two percent by weight, at least three percent by weight, or at least four percent by weight) and/or at most five percent by weight (e.g., at most four percent by weight, at most three percent by weight, at most two percent by weight, at most one percent by weight, at most 0.1 percent by weight, at most 0.01 percent by weight, at most 0.001 percent by weight, or at most 0.0001 percent by weight) of the metal-containing material. In some embodiments, the solution includes from 0.00001 to five (e.g., from 0.0001 to five, from 0.001 to five, from 0.01 to five, from 0.1 to five, from one to five, from 0.0001 to three, from 0.001 to three, from 0.01 to three, from 0.1 to three, from one to three, from 0.0001 to one, from 0.001 to one, from 0.01 to one, from 0.1 to one, from 0.1 to 0.5) percent by weight of one or more metal-containing materials. In some embodiments, the solution includes the metal-containing material at a concentration of at least 1 µg/ml (e.g., at least 5 µg/ml, at least 10 µg/ml, at least 20 µg/ml, at least 30 µg/ml, at least 40 µg/ml, at least 50 µg/ml, or at least 75 µg/ml) and/or at most 100 µg/ml (e.g., at most 75 µg/ml, at most 50 µg/ml, at most 40 µg/ml, at most 30 µg/ml, at most 20 µg/ml, at most 10 µg/ml, or at most 5 µg/ml). In certain embodiments, the solution includes from 1 to 100 (e.g., from 1 to 75, from 1 to 50, from 1 to 25, from 10 to 100, from 10 to 75, from 10 to 50, from 10 to 20) µg of metal-containing material per one ml of the solution. In some embodiments, the concentration of the metal-containing material in a solution is at most the minimum inhibitory concentration for a given bacterium species (e.g., a sporulating bacterium species).

In certain embodiments, the solution containing the material is contacted with the subject relatively soon after formation of the solution. For example, the solution containing the material can be contacted with the subject within about one minute or less (e.g., within about 30 seconds or less, within about 10 seconds or less) of forming the solution. In some embodiments, a longer period of time lapses before the solution containing the material is contacted with the subject. For example a period of time of at least about 1.5 minutes (e.g., at least about five minutes, at least about 10 minutes, at least about 30 minutes, at least about one hour, at least about 10 hours, at least about a day, or at least about a week) lapses between the time the solution containing the material is formed and the solution containing the material is contacted with the subject.

In some embodiments, the metal containing material can be in the form of a foam, a spray, or a drop. The foam, spray, or drop can have the same composition as a solution.

Freeze-Dried Powders

In some embodiments, the metal-containing material can be a freeze-dried powder, formed from freeze-drying a nanodispersion of the metal-containing material that further includes a bulking agent (e.g., mannitol, glycine, gelatin, dextran, glucose, sucrose, and/or lactose) and/or a cryoprotectant (e.g., glycine, glucose, fructose, sucrose, lactose). Without wishing to be bound by theory, it is believed that a bulking agent decreases the likelihood of particle agglomeration, which can occur at high particle concentrations as the solvent is removed by freeze-drying. A cryoprotectant decreases the likelihood of formation of water crystals, which can push the particles into close proximity and increase the likelihood of particle agglomeration. In some embodiments, the freeze-dried powder can be reconstituted into a suspension and/or nanodispersion, for example, by adding water or an aqueous solution and/or by ultrasonicating. In some embodiments, the freeze-dried powder can be incorporated into a pill, capsule, or tablet.

In some embodiments, the freeze-dried powder includes at least 0.01 percent (e.g., at least 0.1 percent, at least one percent, at least five percent, at least ten percent, at least 20 percent, at least 30 percent, or at least 40 percent) by weight and/or at most 50 percent (e.g., at most 40 percent, at most 30 percent, at most 20 percent, at most ten percent, at most five percent, at most one percent, or at most 0.1 percent) by weight of one or more metal-containing materials. In some embodiments, the freeze-dried powder includes from 0.01 to 50 (e.g., from 0.01 to 40, from 0.01 to 20, from one to 20, from one to 40, from ten to 50, from ten to 30, from 20 to 50, from 20 to 30) percent by weight of one or more metal-containing materials.

In some embodiments, the freeze-dried powder includes at least 35 percent by weight (e.g., at least 40 percent, at least 50 percent, at least 60 percent, at least 70 percent, at least 80 percent, or at least 90 percent) and/or at most 99.99 percent (e.g., at most 90 percent, at most 80 percent, at most 70 percent, at most 60 percent, at most 50 percent, or at most 40 percent) by weight of one or more stabilizing agents. In some embodiments, the freeze-dried powder includes from 35 to 99.99 (e.g., from 40 to 80, from 40 to 70, from 50 to 60, from 50 to 75, from 50 to 80) percent by weight of one or more stabilizing agents.

In some embodiments, the freeze-dried powder includes at least 0.01 percent (e.g., at least 0.1 percent, at least one percent, at least five percent, or at least ten percent) by weight and/or at most 15 percent (e.g., at most ten percent, at most five percent, at most one percent, or at most 0.1 percent) by weight of one or more bulking agents and/or cryoprotectants. In some embodiments, the freeze-dried powder includes from 0.01 to 15 (e.g., from 0.01 to ten, from 0.01 to five, from one to 15, from one to ten, from ten to 15) percent by weight of one or more bulking agents and/or cryoprotectants.

Suppositories

In some embodiments, the metal-containing material is in the form of a suppository. The suppository can melt at a physiological temperature and release the metal-containing material at an appropriate location. The suppository can include a suppository base that can melt at physiological temperatures, such as cocoa butter or a hard fat. The suppository also can include a metal-containing material. The metal-containing material can be in the form of a free standing powder or a freeze-dried powder. In some embodiments, the suppository includes at least 70 percent by weight (e.g., at least 75 percent by weight, at least 80 percent by weight, at least 90 percent by weight, at least 95 percent by weight, or at least 97 percent by weight) and/or at most 99.99 percent by weight (at most 97 percent by weight, at most 95 percent by weight, at most 90 percent by weight, at most 80 percent by weight, or at most 75 percent by weight) of a suppository base. In some embodiments, the suppository includes from 70 to 99.99 (e.g., from 70 to 95, from 70 to 90, from 80 to 95, from 80 to 90) percent by weight of a suppository base. In some embodiments, the suppository includes at least 0.01 percent by weight (e.g., at least 3 percent by weight, at least 5 percent by weight, at least 10 percent by weight, at least 20 percent by weight, or at least 25 percent by weight) and/or at most 30 percent by weight (e.g., at most 25 percent by weight, at most 20 percent by weight, at most 10 percent by weight, at most 5 percent by weight, or at most 3 percent by weight) of the metal-containing material. In some embodiments, the suppository includes from 0.01 to 30 (e.g., from 0.01 to 25, from 0.01 to 20, from 0.01 to 10, from three to 20, from three to 30, from three to 10, from 10 to 30, from 10 to 20, from 15 to 20) percent by weight of a suppository base.

Formulation Characteristics

While a controlled-release composition, a cream, a nanodispersion, a solution, a freeze-dried powder, and a suppository have been described in the foregoing, in certain embodiments, the formulation can be in the form of a lotion, a gel, a paste, or an ointment. The lotion can have a lower viscosity than a cream; the gel can be transparent, translucent, and/or opaque, the paste can have more solids than a cream; and an ointment can have low levels of water or be substantially free of water (e.g., about 80% free of water, about 90% free of water, about 95% free of water, about 98% free of water, about 99% free of water, 100% free of water).

In some embodiments, various formulations can optionally include one or more components which can be biologically active or biologically inactive. Examples of components are described above. Further examples of such optional components include base components (e.g., water and/or an oil, such as liquid paraffin, vegetable oil, peanut oil, castor oil, cocoa butter), thickening agents (aluminum stearate, hydrogenated lanolin), gelling agents, dispersing agents, suspending agents, thickening agents, coloring agents, perfumes, excipients (starch, tragacanth, cellulose derivatives, silicones, bentonites, silicic acid, talc), foaming agents (e.g., surfactants), surface active agents, preservatives (e.g., methyl paraben, propyl paraben, benzyl alcohol), and cytoconductive agents (e.g., betaglucan). In certain embodiments, a pharmaceutical carrier composition can include a constituent (e.g., DMSO) to assist in the penetration of skin. In some embodiments, a formulation can include tinting agents, emollients, skin conditioning agents, humectants, preservatives, antioxidants, perfumes, chelating agents: physically and chemically compatible with other components of the composition.

In some embodiments, the metal-containing material can be a preservative. In such embodiments, a form or formulation containing the metal-containing material can be prepared with or without additional preservatives. Moreover, in embodiments in which the metal-containing material acts as a preservative, the metal-containing material may be included in a therapeutic formulation containing other therapeutic agents (e.g., the metal-containing material may be included primarily in certain therapeutic compositions to act as a preservative). Formulations can contain the metal-containing preservative at a concentration of at least 0.01 percent (e.g., at least 0.02 percent, at least 0.05 percent, at least 0.1 percent, or at least percent) and/or at most one percent (at most 0.1 percent, at most 0.05 percent, or at most 0.02 percent). In some embodiments, formulations can contain the metal-containing preservative at a concentration of from 0.01 to one (e.g., from 0.01 to 0.5, from 0.01 to 0.05, from 0.1 to one, from 0.1 to 0.5) percent.

In some embodiments, the formulation decreases the likelihood of discoloration, mirror formation (e.g., silver-mirror formation), and/or viscosity changes, which can occur over time (e.g., one day, two days, five days, one month, two months, three months, six months, a year) when the metal-containing material is mixed with a number of excipients. Without wishing to be bound by theory, it is believed that certain metal ions (e.g., silver ions) are reactive and photosensitive, and can be incompatible with certain excipients and/or form unstable mixtures when incorporated into a formulation. For example, it is believed that in some embodiments, excipients including vicinal diols can induce discoloration by reacting with metals. As an example, a formulation including a metal-containing material (e.g., a silver-containing material) and carboxymethyl cellulose (CMC) can result in discoloration to a dark-colored gel, or a silver-mirror. As an example, a formulation including a nanocrystalline silver, CMC, and propylene glycol (PG) can result in a silver mirror when stored at 40° C. over three weeks. A silver-containing material mixed with CMC and PEG 400 at pH 7.3, stored at 40° C. over three weeks can result in a dark brown formulation.

In some embodiments, the metal-containing material has a dark color, such as a dark brown to black color. Depending on the components of the formulation, the controlled-release composition, cream, foam, gel, lotion, paste, ointment, nanodispersion, solution, spray, drop, or suppository containing the material can be lighter in color than the metal-containing material. For example, a cream containing 2.0% of a nanocrystalline silver material can have a grey color.

In some embodiments, the formulations including the metal-containing material is non-staining to fabrics and/or is easily removed from fabrics. This can be advantageous in order to avoid permanent staining of clothes, for example, when the formulation is for topical use on the skin. The non-staining property is assessed by visually comparing photographs of a fabric prior to staining, after application of a formulation, and after washing the fabric; by measuring a lightness factor of a fabric sample prior to staining with a formulation, after staining, and after washing of the fabric sample using a spectrophotometer (e.g., Color Quest XE, Hunter Associates Laboratory, Inc.); and/or by measuring the level of a metal-containing material remaining in the fabric by analyzing the fabric after laundering using atomic absorption spectroscopy after acid digestion of the fabrics. In some embodiments, a non-staining formulation is such that a fabric stained with the formulation can recover at least 70% (e.g., at least 80%, at least 90%, or at least 95%) of the initial lightness factor, prior to staining.

In some embodiments, depending on the condition to be treated, a cream, lotion, gel, solution, nanodispersion, and/or ointment containing the material can be topically applied, for example, to an area of the skin to relieve skin conditions, such as eczema and/or dry skin conditions.

In some embodiments, depending on the condition to be treated, a solution and/or a nanodispersion containing the material can contact an area having mucous membranes such as mouth, eyes, colon, lungs, and/or other organs, in the form of a rinse, a bath, a wash, an enema, a gargle, a spray, and/or drops, with or without the use of a device. As an example, the solution and/or the nanodispersion can be injected into a subject using a small needle injector and/or a needleless injector. As an another example, the solution and/or the nanodispersion containing the material can be formed into an aerosol (e.g., an aerosol prepared by a mechanical mister, such as a spray bottle or a nebulizer), and the aerosol can be contacted with the subject using an appropriate device (e.g., a hand held inhaler, a mechanical mister, a spray bottle, a nebulizer, an oxygen tent). As a further example, a solution and/or nanodispersion containing the material can be contacted with the subject via a catheter.

In some embodiments, the metal-containing material is in the form of an aerosol or dry powder, formed from lyophilizing, freeze-drying, or drying a nanodispersion. The aerosol or dry powder can be inhaled to contact a respiratory area such as the mouth, lungs, or nasal passage for treatment of respiratory conditions. In some embodiments, the metal-containing material is sub-micron in size.

In some embodiments, the metal-containing material in the form of an article such as a controlled-release composition (e.g., a tablet, pill, capsule or bead having controlled-release properties and/or a controlled-release coating, an enteric-coated tablet, an enteric-coated capsule, an enteric-coated pill, a suspension of enteric-coated beads), a suppository, a solution, a nanodispersion, or a foam can contact the gastrointestinal system of a subject to treat, for example, inflammatory bowel disease (IBD). The article can include a sustained release formulation (e.g., a sustained release capsule) which can allow the metal-containing material to be released at a predetermined rate (e.g., a relatively constant rate). In some embodiments, an article can include a material (e.g., in the form of a coating and/or in the form of a matrix material) that allows the article to pass through certain portions of the gastrointestinal system with relatively little (e.g., no) release of the metal-containing material, but that allows a relatively large amount of the metal-containing material to be released in a desired portion of the gastrointestinal system. As an example, the article can be a controlled-release article (e.g., a tablet, pill, capsule or bead having a controlled-release coating, an enteric-coated tablet, an enteric-coated capsule, an enteric-coated pill, a suspension including an enteric-coated bead) so that the formulation passes through the stomach with little (e.g., no) metal-containing material being released, and so that the metal-containing material is relatively easily released by the article in the intestines. In some embodiments, the article can be an enema or a suppository, which can contact the gastrointestinal system (e.g., the colon) to provide a therapeutic effect.

In some embodiments, the metal-containing formulation (e.g., a cream) is an anti-microbial barrier. In some embodiments, the metal-containing formulation is anti-inflammatory and reduces inflammation in a subject, for example, by suppressing the expression of inflammatory cells. The metal-containing formulation can have enhanced emollient properties such that the formulation can soften and soothe the skin when applied locally. An emollient property is assessed by measuring the extent to which a formulation decreases water evaporation (e.g., from skin). The metal-containing formulation can be substantially free of steroids. The metal-containing formulation can be non-allergenic (e.g., non-allergenic to nuts). In some embodiments, a formulation without metal-containing material, such as a cream, has moisturizing and protecting properties, which can provide therapeutic effects when applied onto an area of a subject. The moisturizing property is measured by a transepidermal water loss (TEWL) test using healthy volunteers (International Research Services Inc (IRSI). Port Chester, N.Y.). In some embodiments, water loss is measured using a Vapometer (Delfin Technologies Ltd., Finland).

In some embodiments, the metal containing formulation has good spreadability, such that the formulation can be spread into a thin layer when topically applied before drying. The spreadability can depend on the viscosity, the melting temperature, the evaporation rate, and/or the solid content of the formulation. For example, in some embodiments, a low viscosity formulation (e.g., viscosity of less than 45,000 cPs) can have a large spreadability and a watery feeling when rubbed into an area of the skin, and a high viscosity (e.g., greater than 2,000,000 cPs) can limit the spreadability of the formulation. The metal-containing formulation can have a viscosity of greater than 60,000 cPs (e.g., greater than 100,000 cPs, greater than 200,000 cPs, greater than 400,000 cPs, greater than 600,000 cPs, greater than 800,000 cPs, greater than 1,000,000 cPs, greater than 1,200,000 cPs, greater than 1,400,000 cPs, or greater than 1,600,000 cPs) and/or less than 2,000,000 cPs (e.g., less than 1,800,000 cPs, less than 1,600,000 cPs, less than 1,400,000 cPs, less than 1,200,000 cPs, less than 1,000,000 cPs, less than 800,000 cPs, less than 600,000 cPs, less than 400,000 cPs, less than 200,000 cPs, or less than 100,000 cPs). Viscosity is measured using a viscometer (e.g., a Brookfield RV II pro viscometer with T-D spindle measured at 1.0 rpm). In some embodiments, a low melting temperature, a low evaporation rate, and/or a low solid content can increase the spreadability of a formulation.

In some embodiments, a metal-containing formulation including metal-containing particles of small particle size (e.g., about 400 nm or less, about 300 nm or less, about 200 nm or less, about 150 nm or less, about 100 nm or less, about 50 nm or less, or about 25 nm or less; and/or about 10 nm or more, about 25 nm or more, about 50 nm or more, about 100 nm or more, about 150 nm or more, about 200 nm or more, or about 300 nm or more) can be more therapeutically effective (e.g., 2× more effective, 5× more effective, 10× more effective, 20× more effective, 50× more effective, 100× more effective) than a metal-containing formulation that does not include metal-containing particles of small particle size, such that a smaller quantity of metal-containing material (e.g., 1/100 of a quantity, 1/50 of a quantity, 1/20 of a quantity, 1/10 of a quantity, 1/5 of a quantity, 1/2 of a quantity) is needed to achieve the same therapeutic effect when the formulation is administered to a subject, for example, to an open wound, past the skin barrier, and/or to a mucosal or serosal area. A decreased quantity of a metal-containing material in a formulation can have decreased toxicological effect on a subject, and can facilitate the administration of a formulation.

In some embodiments, when applied to an area of a subject, the formulation can release a steady amount of a therapeutic agent (e.g., a metal-containing material and/or a non-metal antibiotic medication) over a period of time (e.g., at least 30 minutes, at least one hour, at least two hours, at least three hours, at least six hours, at least 12 hours, or at least 24 hours; and/or at most 48 hours, at most 24 hours, at most 12 hours, at most six hours, at most three hours, at most two hours, or at most one hour). In some embodiments, the period of time is from 30 minutes to 48 hours (e.g., from 30 minutes to 24 hours, from one hour to 24 hours, from six hours to 24 hours). A steady amount refers to an amount that varies by less than 90% (less than 80%, less than 70%, less than 60%) of the initial amount over the period of time.

Mechanism

Without wishing to be bound by theory, it is believed that the therapeutic properties of the metal-containing materials may be explained by one or more potential mechanisms. In one potential mechanism (e.g., at relatively high pH), it is believed that the metal-containing material (e.g., antimicrobial, atomically disordered, nanocrystalline silver-containing materials) forms one or more metastable, relatively high level metal hydroxide species (e.g., $Ag(OH)_4^{3-}$, $Ag(OH)_6^{3-}$) that either directly or indirectly (e.g., via the formation of one or more biological mediators) provide the observed therapeutic properties. In another potential mechanism, it is believed that the metal-containing material is capable of releasing clusters of the metal (e.g., clusters of $Ag^0$, clusters of $Ag^+$, clusters containing both $Ag^+$ and $Ag^0$) that provide the observed therapeutic properties. In a further potential mechanism, it is believed that the concentration of silver in a solution can be raised above the saturation concentration of bare silver ions (e.g., to provide a relatively sustaining reservoir of silver as bare silver ions are consumed). It is believed that, as the bare silver ions are consumed, some of the other silver-containing species can decompose to create additional bare silver ions in accordance with chemical equilibria. It is also believed that the presence of silver in one or more forms other than bare silver ions may raise the level for the effective silver concentration that is nonharmful (e.g., non-toxic) to the cells of a subject (e.g., a human). In an additional potential mechanism, it is believed that one or more forms of silver complexes may be capable of penetrating cellular membranes (e.g., by mimicking species that are normally transported through the membranes), which may accelerate the permeation of silver into the cells. In general, it is believed that the form of the silver-containing species contained in an aqueous solution depends on the solution pH and/or the concentrations of the various silver-containing species in the solid form of the silver-containing material. It is believed that, in general, at low pH the dominant species is a bare silver ion, but that at higher pH, where the solubility of bare silver ions is believed to be limited by the solubility of silver hydroxide, other types of species including complexed silver ions and/or silver-containing clusters become increasingly stable provided that the concentration of bare silver ions remains at the saturation concentration. It is also believed that the nature and relative population of the silver-containing species can depend on the rate at which the species can dissolve from the solid silver-bearing material and the rate at which the species can react with one another in the solution. It is believed that combinations of potential mechanisms may result in the observed therapeutic effect of the metal-containing material.

Without wishing to be bound by theory, it is believed that in some embodiments, a metal-containing material can inhibit bacterial matrix formation, for example, in a biofilm. In some embodiments, the metal-containing material can decrease the amount of ATP available to a microbe for inhibition or microbicidal purposes.

Without wishing to be bound by theory, it is believed that a metal-containing material is sporicidal because the metal-containing material is chemically reactive with thiol and imidazole groups. Therefore, it is possible that the metal-containing material can attack a broad range of molecular targets on both the vegetative cells and the spores of sporulating bacteria, and possibly even the exotoxins secreted by the bacteria. Additionally, as spore germination is sensitive to thiol groups, a metal-containing material may be able to interfere with the germination process itself.

In general, clusters refer to relatively small groups of atoms, ions or the like. For example, a cluster can contain at least two (e.g., at least three, at least four, at least five, at least six, at least seven, at least eight, at least nine, at least 10, at least 11, at least 12, at least 13, at least 14, at least 15, at least 20, at least 30, at least 40, at least 50, at least 60, at least 70, at least 80, or at least 90) atoms, ions or the like, and/or at most 1,000 (e.g., at most 900, at most 800, at most 700, at most 600, at most 500, at most 400, at most 300, at most 200, or at most 100) atoms, ions or the like. Clusters are described, for example, in R. P. Andres et al., "Research Opportunities on Cluster and Cluster-Assembled Materials", J. Mater. Res. Vol. 4, No 3, 1989, p. 704. In certain embodiments, a cluster (e.g., a cluster containing silver) can contain less than the 14 atoms and have a normal face centered cubic crystal lattice.

Materials

The metal-containing material can be an ionic material or a non-ionic material. The metal-containing material can be, for example, an atom, a molecule, or a cluster. In general, the metal-containing material is a metal or an alloy. Examples of metal elements that can be contained in metal-containing materials include Group I A metal elements (e.g., Li and others), Group II A metal elements (e.g., Be and others), Group III A metal elements (e.g., Sc and others), Group IV A metal elements (e.g., Ti and others), Group V A metal elements (e.g., V and others), Group VI A metal elements (e.g., Cr and others), Group VII A metal elements (e.g., Mn and others), Group VIII A metal elements (e.g., Fe, Co, Ni and others), Group I B metal elements (e.g., Cu and others), Group II B metal elements (e.g., Zn and others), members of the lanthanide metal element series (e.g., La and others), and members of the actinide metal element series (e.g., Ac and others). In certain embodiments, metal-containing materials contain silver, gold, platinum, palladium, copper, and/or zinc. In some embodiments, a metal-containing material can include one or more transition metal elements (e.g., scandium, titanium, vanadium, chromium, manganese, iron, cobalt, nickel, copper and/or zinc). As an example, a metal-containing material can contain silver and platinum.

Examples of silver-containing materials include silver oxide, colloidal silver, silver nitrate and silver sulfadiazine, silver carbonate, silver acetate, silver lactate, silver citrate, silver hydroxide, silver succinate, silver chlorate, silver stearate, silver sorbate, silver oleate, silver gluconate, silver glycolate, silver adipate, silver myristate, silver benzoate, silver methanesulfonate, silver trifluoracetate, silver trifluoromethanesulfonate, silver behenate, silver phthalate, silver oxalate, silver sulfonate, and alkali silver thiosulphate (e.g., sodium silver thiosulphate, potassium silver thiosulphate).

In addition to one or more metal elements, a metal-containing material can contain, for example, oxygen, nitrogen, carbon, boron, sulfur, phosphorus, silicon, a halogen (e.g., fluorine, chlorine, bromine, iodine) and/or hydrogen. Examples of such metal-containing materials include metal oxides, metal hydroxides, metal nitrides, metal carbides, metal phosphides, metal silicates, metal borides, metal sulfides, metal halides (e.g., metal fluorides, metal chlorides, metal bromides, metal iodides), metal myristates, metal sorbates, metal stearates, metal oleates, metal gluconates, metal glycolates, metal adipates, metal silicates, metal phosphides, metal hydrides, metal nitrates, metal carbonates, metal sulfadiazines, metal hydrides, metal acetates, metal lactates, metal citrates, metal benzoate, metal methanesulfonate, metal trifluoracetate, metal trifluoromethanesulfonate, metal behenate, metal phthalate, metal oxalate, metal sulfonate, alkali metal thiosulphates (e.g., sodium metal thiosulphate, potassium metal thiosulphate). In certain embodiments, a metal-containing material contains at least about one atomic percent (e.g., at least about three atomic percent, at least about five atomic percent, at least about 10 atomic percent, at least about 20 atomic percent, at least about 30 atomic percent, at least about 40 atomic percent, or at least about 50 atomic percent) and/or at most about 90 atomic percent (e.g., at most about 80 atomic percent, at most about 70 atomic percent, at most about 60 atomic percent, at most about 50 atomic percent, at most about 40 atomic percent, at most about 30 atomic percent, at most about 20 atomic percent, at most about 15 atomic percent, at most about 12 atomic percent, or at most about 10 atomic percent) of nonmetallic elements. For example, in some embodiments, a silver-containing material can contain oxygen in an amount from about five atomic percent to about 20 atomic percent (e.g., from about five atomic percent to about 15 atomic percent, from about eight atomic percent to about 12 atomic percent).

In certain embodiments, the metal-containing materials are an antimicrobial material, an anti-biofilm, an antibacterial material, an anti-inflammatory material, an antifungal material, an antiviral material, an anti-autoimmune material, an anti-cancer material, an MMP modulating material, an atomically disordered crystalline material, and/or a nanocrystalline material.

As used herein, an antimicrobial material herein refers to a material that has sufficient antimicrobial activity to have a beneficial therapeutic effect. In certain embodiments, an antimicrobial material has a corrected zone of inhibition ("CZOI"; defined here as the size of the zone of bacterial growth inhibition corrected so as to not include the size of the antimicrobial test sample creating the zone) of at least about two millimeters (e.g., at least about three millimeters, at least about four millimeters, at least about five millimeters, at least about six millimeters, at least about seven millimeters, at least about eight millimeters, at least about nine millimeters, or at least about 10 millimeters). The CZOI of a material is determined as follows. The material is formed as a coating on a dressing (see discussion below), or as a controlled-release composition, a metal-containing dispersion, a solution, a cream, or a gel. The zone of inhibition method is done by streaking bacteria onto Petri dish full of nutrient-containing agar. Bacteria are streaked using a sterile cotton swab, making sure the entire plate is covered to produce a bacterial lawn. Plates are then allowed to dry about 10 min prior to adding test samples. After allowing the bacteria to dry on the plate for about 10 minutes, test samples (e.g. silver coated dressing or devices) are placed onto the Petri dish surface. Plates are then incubated inverted at 32.5° C. for 18-24 hours. Plates are examined following the incubation period by measuring inhibitory zones produced around the test sample. For testing solutions, dispersions, creams, or gels, the standard assay is modified by the creation of 5-mm wells in the agar plates. More than one sample can be tested on each plate providing the wells were placed far enough apart from each other that the zones do not overlap. In most cases 3-4 holes are punched on each plate to the full depth of the agar using a sterilized #3 brass cork bore, creating wells approximately 5 mm in diameter. Bacteria are then streaked onto the plate using a sterile cotton swab, making sure the entire plate is covered to produce a bacterial lawn. Plates are then allowed to dry about 10 min prior to adding test samples. After allowing the bacteria to dry on the plate for about 10 minutes, the silver creams or placebo creams are added using aseptic technique. Creams were put into sterile 3 mL syringes. Each well is filled completely with the corresponding silver cream, approximately 0.1 milliliter. Plates are then incubated inverted at 32.5° C. for 18-24 hours. Plates are examined following the incubation period by measuring inhibitory zones produced around the wells. When testing a solid test material (e.g., a dressing), the zone of inhibition ("ZOI") is measured and the CZOI is calculated as the ZOI minus the diameter of the test material in contact with the agar. It is to be noted that, while this test for antimicrobial properties is performed on materials that are in the form of a coating on a substrate (e.g., in the form of a dressing), antimicrobial materials are not limited to materials that are coated on a substrate. Rather, a material in any form may be antimicrobial, but it is in the form of a coating on a substrate (e.g., in the form of a dressing) when its antimicrobial properties are tested according to the procedure described herein. When testing a liquid, sol, of gel test material (e.g., a cream), the zone of inhibition ("ZOI") is measured so as to include the diameter of the well containing the test sample (that is, the ZOI is NOT corrected).

As referred to herein, an atomically disordered, crystalline material (e.g., an atomically disordered, nanocrystalline material) means a material that has more long range ordered, crystalline structure (a lesser degree of defects) than the material has in a fully amorphous state, but that also has less long range, ordered crystalline structure (a higher degree of defects) than the material has in a bulk crystalline state, such as in the form of a cast, wrought or plated material. Examples of defects include point defects, vacancies, line defects, grain boundaries, subgrain boundaries and amorphous regions. Point defects are defects on a size scale of no more than about four atomic spacings. A vacancy is the omission of an atom from its regular atomic site in the crystal lattice. Line defects are defective regions (e.g., edge dislocations, screw dislocations) that result in lattice distortions along a line (which may or may not be a straight line), and generally have a longer scale than point defects. In an edge dislocation, a lattice displacement is produced by a plane of atoms that forms a terminus of the lattice. In a screw dislocation, part of the lattice is displaced with respect to an adjacent part of the lattice. Grain boundaries separate regions having different crystallographic orientation or misorientation (e.g., high angle grain boundaries, low angle grain boundaries, including tilt boundaries and twist boundaries). Subgrain boundaries refer to low angle grain boundaries. An amorphous region is a region that does not exhibit long range, ordered crystalline structure. In certain embodiments, an atomically disordered, crystalline material (e.g., an atomically disordered, nanocrystalline material) has a degree of atomic disorder that is about the same as the degree of atomic disorder of the nanocrystalline silver coating of a member of the Acticoat™ family of dressings (Smith & Nephew, Hull, UK) (e.g., an Acticoat™ dressing, an Acticoat7™ dressing, an Acticoat™ moisture coating dressing, an Acticoat™ absorbent dressings). In some embodiments, an atomically disordered, crystalline material (e.g., an atomically disordered, nanocrystalline material) has a degree of atomic disorder that is about the same as the degree of atomic disorder of the nanocrystalline silver coatings having a CZOI of at least five millimeters that are disclosed in the examples of Burrell et al., U.S. Pat. No. 5,958,440. In certain embodiments, an atomically disordered, crystalline material (e.g., an atomically disordered, nanocrystalline material), when contacted with an alcohol or water-based electrolyte, is released into the alcohol or water-based electrolyte (e.g., as ions, atoms, molecules and/or clusters) over a time scale of at least about one hour (e.g., at least about two hours, at least about 10 hours, or at least about a day). Examples of alcohols and/or water-based electrolytes include body fluids (e.g., blood, urine, saliva) and body tissue (e.g., skin, muscle, bone).

As referred to herein, a nanocrystalline material is a single-phase polycrystal or a multi-phase polycrystal having a maximum dimension of about 100 nanometers or less (e.g., about 90 nanometers or less, about 80 nanometers or less, about 70 nanometers or less, about 60 nanometers or less, about 50 nanometers or less, about 40 nanometers or less, about 30 nanometers or less, about 25 nanometers or less) in at least one dimension.

Examples of antimicrobial metal-containing materials (which may or may not also be an atomically disordered crystalline material or a nanocrystalline material) include antimicrobial silver-containing materials (e.g., antimicrobial silver, antimicrobial silver alloys, antimicrobial silver oxides, antimicrobial silver carbides, antimicrobial silver nitrides, antimicrobial silver borides, antimicrobial silver sulfides, antimicrobial silver myristates, antimicrobial silver stearates, antimicrobial silver oleates, antimicrobial silver gluconates, antimicrobial silver glycolates, antimicrobial silver adipates, antimicrobial silver silicates, antimicrobial silver phosphides, antimicrobial silver halides, antimicrobial silver hydrides, antimicrobial silver nitrates, antimicrobial silver carbonates, antimicrobial silver sulfadiazines, antimicrobial silver acetates, antimicrobial silver lactates, antimicrobial silver citrates, antimicrobial silver benzoate, antimicrobial silver methanesulfonate, antimicrobial silver trifluoracetate, antimicrobial silver trifluoromethanesulfonate, antimicrobial silver behenate, antimicrobial silver phthalate, antimicrobial silver oxalate, antimicrobial silver sulfonate, antimicrobial alkali silver thiosulphates (e.g., antimicrobial sodium silver thiosulphate, antimicrobial potassium silver thiosulphate)), antimicrobial gold-containing materials (e.g., antimicrobial gold, antimicrobial gold alloys, antimicrobial gold oxides, antimicrobial gold carbides, antimicrobial gold nitrides, antimicrobial gold borides, antimicrobial gold sulfides, antimicrobial gold myristates, antimicrobial gold stearates, antimicrobial gold oleates, antimicrobial gold gluconates, antimicrobial gold glycolates, antimicrobial gold adipates, antimicrobial gold silicates, antimicrobial gold phosphides, antimicrobial gold halides, antimicrobial gold hydrides, antimicrobial gold nitrates, antimicrobial gold carbonates, antimicrobial gold sulfadiazines, antimicrobial gold acetates, antimicrobial gold lactates, antimicrobial gold citrates, antimicrobial gold benzoate, antimicrobial gold methanesulfonate, antimicrobial gold trifluoracetate, antimicrobial gold trifluoromethanesulfonate, antimicrobial gold behenate, antimicrobial gold phthalate, antimicrobial gold oxalate, antimicrobial gold sulfonate, antimicrobial alkali gold thiosulphates (e.g., antimicrobial sodium gold thiosulphate, antimicrobial potassium gold thiosulphate)), antimicrobial platinum-containing materials (e.g., antimicrobial platinum, antimicrobial platinum alloys, antimicrobial platinum oxides, antimicrobial platinum carbides, antimicrobial platinum nitrides, antimicrobial platinum borides, antimicrobial platinum sulfides, antimicrobial platinum myristates, antimicrobial platinum stearates, antimicrobial platinum oleates, antimicrobial platinum gluconates, antimicrobial platinum glycolates, antimicrobial platinum adipates, antimicrobial platinum silicates, antimicrobial platinum phosphides, antimicrobial platinum halides, antimicrobial platinum hydrides, antimicrobial platinum nitrates, antimicrobial platinum carbonates, antimicrobial platinum sulfadiazines, antimicrobial platinum acetates, antimicrobial platinum lactates, antimicrobial platinum citrates, antimicrobial platinum benzoate, antimicrobial platinum methanesulfonate, antimicrobial platinum trifluoracetate, antimicrobial platinum trifluoromethanesulfonate, antimicrobial platinum behenate, antimicrobial platinum phthalate, antimicrobial platinum oxalate, antimicrobial platinum sulfonate, antimicrobial alkali platinum thiosulphates (e.g., antimicrobial sodium platinum thiosulphate, antimicrobial potassium platinum thiosulphate)), antimicrobial palladium-containing materials (e.g., antimicrobial palladium, antimicrobial palladium alloys, antimicrobial palladium oxides, antimicrobial palladium carbides, antimicrobial palladium nitrides, antimicrobial palladium borides, antimicrobial palladium sulfides, antimicrobial palladium myristates, antimicrobial palladium stearates, antimicrobial palladium oleates, antimicrobial palladium gluconates, antimicrobial palladium glycolates, antimicrobial palladium adipates, antimicrobial palladium silicates, antimicrobial palladium phosphides, antimicrobial palladium halides, antimicrobial palladium hydrides, antimicrobial palladium nitrates, antimicrobial palladium carbonates, antimicrobial palladium sulfadiazines, antimicrobial palladium acetates, antimicrobial palladium lactates, antimicrobial palladium citrates, antimicrobial palladium benzoate, antimicrobial palladium methanesulfonate, antimicrobial palladium trifluoracetate, antimicrobial palladium trifluoromethanesulfonate, antimicrobial palladium behenate, antimicrobial palladium phthalate, antimicrobial palladium oxalate, antimicrobial palladium sulfonate, and/or antimicrobial alkali palladium thiosulphates (e.g., antimicrobial sodium palladium thiosulphate, antimicrobial potassium palladium thiosulphate)), antimicrobial zinc-containing materials (e.g., antimicrobial zinc, antimicrobial zinc alloys, antimicrobial zinc oxides, antimicrobial zinc carbides, antimicrobial zinc nitrides, antimicrobial zinc borides, antimicrobial zinc sulfides, antimicrobial zinc myristates, antimicrobial zinc stearates, antimicrobial zinc oleates, antimicrobial zinc gluconates, antimicrobial zinc glycolates, antimicrobial zinc adipates, antimicrobial zinc silicates, antimicrobial zinc phosphides, antimicrobial zinc halides, antimicrobial zinc hydrides, antimicrobial zinc nitrates, antimicrobial zinc carbonates, antimicrobial zinc sulfides, antimicrobial zinc sulfadiazines, antimicrobial zinc acetates, antimicrobial zinc lactates, antimicrobial zinc citrates, antimicrobial zinc benzoate, antimicrobial zinc methanesulfonate, antimicrobial zinc trifluoracetate, antimicrobial zinc trifluoromethanesulfonate, antimicrobial zinc behenate, antimicrobial zinc phthalate, antimicrobial zinc oxalate, antimicrobial zinc sulfonate), antimicrobial copper-containing materials (e.g., antimicrobial copper, antimicrobial copper alloys, antimicrobial copper oxides, antimicrobial copper carbides, antimicrobial copper nitrides, antimicrobial copper borides, antimicrobial copper sulfides, antimicrobial copper myristates, antimicrobial copper stearates, antimicrobial copper oleates, antimicrobial copper gluconates, antimicrobial copper glycolates, antimicrobial copper adipates, antimicrobial copper silicates, antimicrobial copper phosphides, antimicrobial copper halides, antimicrobial copper hydrides, antimicrobial copper nitrates, antimicrobial copper carbonates, antimicrobial copper sulfides, antimicrobial copper sulfadiazines, antimicrobial copper acetates, antimicrobial copper lactates, antimicrobial copper citrates, antimicrobial copper benzoate, antimicrobial copper methanesulfonate, antimicrobial copper trifluoracetate, antimicrobial copper trifluoromethanesulfonate, antimicrobial copper behenate, antimicrobial copper phthalate, antimicrobial copper oxalate, antimicrobial copper sulfonate, antimicrobial alkali copper thiosulphates (e.g., antimicrobial sodium copper thiosulphate, antimicrobial potassium copper thiosulphate)).

While the preceding paragraph lists certain metal-containing materials that are anti-microbial, similar metal-containing materials (oxides, carbides, nitrides, borides, sulfides, myristates, stearates, oleates, gluconates, glycolates, adipates, silicates, phosphides, halides, hydrides, nitrates, hydroxides, carbonates, sulfides, sulfadiazines, acetates, lactates, citrates, benzoates, methanesulfonates, trifluoracetates, trifluoromethanesulfonates, behenates, phthalates, oxalates, sulfonates, and/or alkali metal thiosulphates of silver, gold, palladium, and/or platinum can be anti-biofilm materials, antibacterial (e.g., antibacterial, anti-bacterial spore) materials, anti-inflammatory materials, antifungal materials, antiviral materials, anti-autoimmune materials, anti-cancer materials, and/or MMP modulating materials.

Examples of nanocrystalline metal-containing materials (which may or may not also be an antimicrobial material or an atomically disordered crystalline material) include nanocrystalline silver-containing materials (e.g., nanocrystalline silver, nanocrystalline silver alloys, nanocrystalline silver oxides, nanocrystalline silver carbides, nanocrystalline silver nitrides, nanocrystalline silver borides, nanocrystalline silver sulfides, nanocrystalline silver halides, nanocrystalline silver myristates, nanocrystalline silver stearates, nanocrystalline silver oleates, nanocrystalline silver gluconates, nanocrystalline silver glycolates, nanocrystalline silver adipates, nanocrystalline silver silicates, nanocrystalline silver phosphides, nanocrystalline silver hydrides, nanocrystalline silver nitrates, nanocrystalline silver carbonates, nanocrystalline silver sulfides, nanocrystalline silver sulfadiazines, nanocrystalline silver acetates, nanocrystalline silver lactates, nanocrystalline silver citrates, nanocrystalline silver benzoate, nanocrystalline silver methanesulfonate, nanocrystalline silver trifluoracetate, nanocrystalline silver trifluoromethanesulfonate, nanocrystalline silver behenate, nanocrystalline silver phthalate, nanocrystalline silver oxalate, nanocrystalline silver sulfonate, nanocrystalline alkali silver thiosulphates (e.g., nanocrystalline sodium silver thiosulphate, nanocrystalline potassium silver thiosulphate)), nanocrystalline gold-containing materials (e.g., nanocrystalline gold, nanocrystalline gold alloys, nanocrystalline gold oxides, nanocrystalline gold carbides, nanocrystalline gold nitrides, nanocrystalline gold borides, nanocrystalline gold sulfides, nanocrystalline gold halides, nanocrystalline gold hydrides, nanocrystalline gold nitrates, nanocrystalline gold myristates, nanocrystalline gold stearates, nanocrystalline gold oleates, nanocrystalline gold gluconates, nanocrystalline gold glycolates, nanocrystalline gold adipates, nanocrystalline gold silicates, nanocrystalline gold phosphides, nanocrystalline gold carbonates, nanocrystalline gold sulfides, nanocrystalline gold sulfadiazines, nanocrystalline gold acetates, nanocrystalline gold lactates, nanocrystalline gold citrates, nanocrystalline gold benzoate, nanocrystalline gold methanesulfonate, nanocrystalline gold trifluoracetate, nanocrystalline gold trifluoromethanesulfonate, nanocrystalline gold behenate, nanocrystalline gold phthalate, nanocrystalline gold oxalate, nanocrystalline gold sulfonate, nanocrystalline alkali gold thiosulphates (e.g., nanocrystalline sodium gold thiosulphate, nanocrystalline potassium gold thiosulphate)), nanocrystalline platinum-containing materials (e.g., nanocrystalline platinum, nanocrystalline platinum alloys, nanocrystalline platinum oxides, nanocrystalline platinum carbides, nanocrystalline platinum nitrides, nanocrystalline platinum borides, nanocrystalline platinum sulfides, nanocrystalline platinum myristates, nanocrystalline platinum stearates, nanocrystalline platinum oleates, nanocrystalline platinum gluconates, nanocrystalline platinum glycolates, nanocrystalline platinum adipates, nanocrystalline platinum silicates, nanocrystalline platinum phosphides, nanocrystalline platinum halides, nanocrystalline platinum hydrides, nanocrystalline platinum nitrates, nanocrystalline platinum carbonates, nanocrystalline platinum sulfides, nanocrystalline platinum sulfadiazines, nanocrystalline platinum acetates, nanocrystalline platinum lactates, nanocrystalline platinum citrates, nanocrystalline platinum benzoate, nanocrystalline platinum methanesulfonate, nanocrystalline platinum trifluoracetate, nanocrystalline platinum trifluoromethanesulfonate, nanocrystalline platinum behenate, nanocrystalline platinum phthalate, nanocrystalline platinum oxalate, nanocrystalline platinum sulfonate, nanocrystalline alkali platinum thiosulphates (e.g., nanocrystalline sodium platinum thiosulphate, nanocrystalline potassium platinum thiosulphate)), nanocrystalline palladium-containing materials (e.g., nanocrystalline palladium, nanocrystalline palladium alloys, nanocrystalline palladium oxides, nanocrystalline palladium carbides, nanocrystalline palladium nitrides, nanocrystalline palladium borides, nanocrystalline palladium sulfides, nanocrystalline palladium myristates, nanocrystalline palladium stearates, nanocrystalline palladium oleates, nanocrystalline palladium glycolates, nanocrystalline palladium gluconates, nanocrystalline palladium adipates, nanocrystalline palladium silicates, nanocrystalline palladium phosphides, nanocrystalline palladium halides, nanocrystalline palladium hydrides, nanocrystalline palladium nitrates, nanocrystalline palladium carbonates, nanocrystalline palladium sulfides, nanocrystalline palladium sulfadiazines, nanocrystalline palladium acetates, nanocrystalline palladium lactates, nanocrystalline palladium citrates, nanocrystalline palladium benzoate, nanocrystalline palladium methanesulfonate, nanocrystalline palladium trifluoracetate, nanocrystalline palladium trifluoromethanesulfonate, nanocrystalline palladium behenate, nanocrystalline palladium phthalate, nanocrystalline palladium oxalate, nanocrystalline palladium sulfonate, nanocrystalline alkali palladium thiosulphates (e.g., nanocrystalline sodium palladium thiosulphate, nanocrystalline potassium palladium thiosulphate)), nanocrystalline zinc-containing materials (e.g., nanocrystalline zinc, nanocrystalline zinc alloys, nanocrystalline zinc oxides, nanocrystalline zinc carbides, nanocrystalline zinc nitrides, nanocrystalline zinc borides, nanocrystalline zinc sulfides, nanocrystalline zinc myristates, nanocrystalline zinc stearates, nanocrystalline zinc oleates, nanocrystalline zinc gluconates, nanocrystalline zinc glycolates, nanocrystalline zinc adipates, nanocrystalline zinc silicates, nanocrystalline zinc phosphides, nanocrystalline zinc halides, nanocrystalline zinc hydrides, nanocrystalline zinc nitrates, nanocrystalline zinc carbonates, nanocrystalline zinc sulfides, nanocrystalline zinc sulfadiazines, nanocrystalline zinc acetates, nanocrystalline zinc lactates, nanocrystalline zinc citrates, nanocrystalline zinc benzoate, nanocrystalline zinc methanesulfonate, nanocrystalline zinc trifluoracetate, nanocrystalline zinc trifluoromethanesulfonate, nanocrystalline zinc behenate, nanocrystalline zinc phthalate, nanocrystalline zinc oxalate, nanocrystalline zinc sulfonate), nanocrystalline copper-containing materials (e.g., nanocrystalline copper, nanocrystalline copper alloys, nanocrystalline copper oxides, nanocrystalline copper carbides, nanocrystalline copper nitrides, nanocrystalline copper borides, nanocrystalline copper sulfides, nanocrystalline copper myristates, nanocrystalline copper stearates, nanocrystalline copper oleates, nanocrystalline copper gluconates, nanocrystalline copper glycolates, nanocrystalline copper adipates, nanocrystalline copper silicates, nanocrystalline copper phosphides, nanocrystalline copper halides, nanocrystalline copper hydrides, nanocrystalline copper nitrates, nanocrystalline copper carbonates, nanocrystalline copper sulfadiazines, nanocrystalline copper acetates, nanocrystalline copper lactates, nanocrystalline copper citrates, nanocrystalline copper benzoate, nanocrystalline copper methanesulfonate, nanocrystalline copper trifluoracetate, nanocrystalline copper trifluoromethanesulfonate, nanocrystalline copper behenate, nanocrystalline copper phthalate, nanocrystalline copper oxalate, nanocrystalline copper sulfonate, nanocrystalline alkali copper thiosulphates (e.g., nanocrystalline sodium copper thiosulphate, nanocrystalline potassium copper thiosulphate)).

Examples of atomically disordered, crystalline metal-containing material (which may or may not also be an antimicrobial material or a nanocrystalline material) include atomically disordered, crystalline silver-containing materials (e.g., atomically disordered, crystalline silver; atomically disordered, crystalline silver alloys; atomically disordered, crystalline silver oxides; atomically disordered, crystalline silver carbides; atomically disordered, crystalline silver nitrides; atomically disordered, crystalline silver borides; atomically disordered, crystalline silver sulfides; atomically disordered, crystalline silver myristates; atomically disordered, crystalline silver stearates; atomically disordered, crystalline silver oleates; atomically disordered, crystalline silver gluconates; atomically disordered, crystalline silver glycolates; atomically disordered, crystalline silver adipates; atomically disordered, crystalline silver silicates; atomically disordered, crystalline silver phosphides; atomically disordered, crystalline silver halides; atomically disordered, crystalline silver hydrides; atomically, crystalline silver nitrates; atomically disordered, crystalline silver carbonates; atomically disordered, crystalline silver sulfides; atomically disordered, crystalline silver sulfadiazines; atomically disordered, crystalline silver acetates; atomically disordered, crystalline silver lactates; atomically disordered, crystalline silver citrates; atomically disordered, crystalline silver benzoate; atomically disordered, crystalline silver methanesulfonate; atomically disordered, crystalline silver trifluoracetate; atomically disordered, crystalline silver trifluoromethanesulfonate; atomically disordered, crystalline silver behenate; atomically disordered, crystalline silver phthalate; atomically disordered, crystalline silver oxalate; atomically disordered, crystalline silver sulfonate; atomically disordered, crystalline alkali silver thiosulphates (e.g., atomically disordered, crystalline sodium silver thiosulphate, atomically disordered, crystalline potassium silver thiosulphate)), atomically disordered, crystalline gold-containing materials (atomically disordered, crystalline gold; atomically disordered, crystalline gold alloys; atomically disordered, crystalline gold oxides; atomically disordered, crystalline gold carbides; atomically disordered, crystalline gold nitrides; atomically disordered, crystalline gold borides; atomically disordered, crystalline gold sulfides; atomically disordered, crystalline gold myristates; atomically disordered, crystalline gold stearates; atomically disordered, crystalline gold oleates; atomically disordered, crystalline gold gluconates; atomically disordered, crystalline gold glycolates; atomically disordered, crystalline gold adipates; atomically disordered, crystalline gold silicates; atomically disordered, crystalline gold phosphides; atomically disordered, crystalline gold halides; atomically disordered, crystalline gold hydrides, atomically disordered, crystalline gold nitrates; atomically disordered, crystalline gold carbonates; atomically disordered, crystalline gold sulfides; atomically disordered, crystalline gold sulfadiazines; atomically disordered, crystalline gold acetates; atomically disordered, crystalline gold lactates; atomically disordered, crystalline gold citrates; atomically disordered, crystalline gold benzoate; atomically disordered, crystalline gold methanesulfonate; atomically disordered, crystalline gold trifluoracetate; atomically disordered, crystalline gold trifluoromethanesulfonate; atomically disordered, crystalline gold behenate; atomically disordered, crystalline gold phthalate; atomically disordered, crystalline gold oxalate; atomically disordered, crystalline gold sulfonate; atomically disordered, crystalline alkali gold thiosulphates (e.g., atomically disordered, crystalline sodium gold thiosulphate, atomically disordered, crystalline potassium gold thiosulphate)), atomically disordered, crystalline platinum-containing materials (e.g., atomically disordered, crystalline platinum; atomically disordered, crystalline platinum alloys; atomically disordered, crystalline platinum oxides; atomically disordered, crystalline platinum carbides; atomically disordered, crystalline platinum nitrides; atomically disordered, crystalline platinum borides; atomically disordered, crystalline platinum sulfides; atomically disordered, crystalline platinum myristates; atomically disordered, crystalline platinum stearates; atomically disordered, crystalline platinum oleates; atomically disordered, crystalline platinum gluconates; atomically disordered, crystalline platinum glycolates; atomically disordered, crystalline platinum adipates; atomically disordered, crystalline platinum silicates; atomically disordered, crystalline platinum phosphides; atomically disordered, crystalline platinum halides; atomically disordered, crystalline platinum hydrides, atomically disordered, crystalline platinum nitrates; atomically disordered, crystalline platinum carbonates; atomically disordered, crystalline platinum sulfides; atomically disordered, crystalline platinum sulfadiazines; atomically disordered, crystalline platinum acetates; atomically disordered, crystalline platinum lactates; atomically disordered, crystalline platinum citrates; atomically disordered, crystalline platinum benzoate; atomically disordered, crystalline platinum methanesulfonate; atomically disordered, crystalline platinum trifluoracetate; atomically disordered, crystalline platinum trifluoromethanesulfonate; atomically disordered, crystalline platinum behenate; atomically disordered, crystalline platinum phthalate; atomically disordered, crystalline platinum oxalate; atomically disordered, crystalline platinum sulfonate; atomically disordered, crystalline alkali platinum thiosulphates (e.g., atomically disordered, crystalline sodium platinum thiosulphate, atomically disordered, crystalline potassium platinum thiosulphate), atomically disordered, crystalline palladium-containing materials (e.g., atomically disordered, crystalline palladium; atomically disordered, crystalline palladium alloys; atomically disordered, crystalline palladium oxides; atomically disordered, crystalline palladium carbides; atomically disordered, crystalline palladium nitrides; atomically disordered, crystalline palladium borides; atomically disordered, crystalline palladium sulfides; atomically disordered, crystalline palladium myristates; atomically disordered, crystalline palladium stearates; atomically disordered, crystalline palladium oleates; atomically disordered, crystalline palladium gluconates; atomically disordered, crystalline palladium glycolates; atomically disordered, crystalline palladium adipates; atomically disordered, crystalline palladium silicates; atomically disordered, crystalline palladium phosphides; atomically disordered, crystalline palladium halides; atomically disordered, crystalline palladium hydrides, atomically disordered, crystalline palladium nitrates; atomically disordered, crystalline palladium carbonates; atomically disordered, crystalline palladium sulfides; atomically disordered, crystalline palladium sulfadiazines; atomically disordered, crystalline palladium acetates; atomically disordered, crystalline palladium lactates; atomically disordered, crystalline palladium citrates; atomically disordered, crystalline palladium benzoate; atomically disordered, crystalline palladium methanesulfonate; atomically disordered, crystalline palladium trifluoracetate; atomically disordered, crystalline palladium trifluoromethanesulfonate; atomically disordered, crystalline palladium behenate; atomically disordered, crystalline palladium phthalate; atomically disordered, crystalline palladium oxalate; atomically disordered, crystalline palladium sulfonate; atomically disordered, crystalline alkali palladium thiosulphates (e.g., atomically disordered, crystalline sodium palladium thiosulphate, atomically disordered, crystalline potassium palladium thiosulphate)), atomically disordered, crystalline zinc-containing materials (e.g., atomically disordered, crystalline zinc; atomically disordered, crystalline zinc alloys; atomically disordered, crystalline zinc oxides; atomically disordered, crystalline zinc carbides; atomically disordered, crystalline zinc nitrides; atomically disordered, crystalline zinc borides; atomically disordered, crystalline zinc sulfides; atomically disordered, crystalline zinc myristates; atomically disordered, crystalline zinc stearates; atomically disordered, crystalline zinc oleates; atomically disordered, crystalline zinc gluconates; atomically disordered, crystalline zinc glycolates; atomically disordered, crystalline zinc adipates; atomically disordered, crystalline zinc silicates; atomically disordered, crystalline zinc phosphides; atomically disordered, crystalline zinc halides; atomically disordered, crystalline zinc hydrides, atomically disordered, crystalline zinc nitrates; atomically disordered, crystalline zinc carbonates; atomically disordered, crystalline zinc sulfides; atomically disordered, crystalline zinc sulfadiazines; atomically disordered, crystalline zinc acetates; atomically disordered, crystalline zinc lactates; atomically disordered, crystalline zinc citrates; atomically disordered, crystalline zinc benzoate; atomically disordered, crystalline zinc methanesulfonate; atomically disordered, crystalline zinc trifluoracetate; atomically disordered, crystalline zinc trifluoromethanesulfonate; atomically disordered, crystalline zinc behenate; atomically disordered, crystalline zinc phthalate; atomically disordered, crystalline zinc oxalate; atomically disordered, crystalline zinc sulfonate), atomically disordered, crystalline copper-containing materials (e.g., atomically disordered, crystalline copper; atomically disordered, crystalline copper alloys; atomically disordered, crystalline copper oxides; atomically disordered, crystalline copper carbides; atomically disordered, crystalline copper nitrides; atomically disordered, crystalline copper borides; atomically disordered, crystalline copper sulfides; atomically disordered, crystalline copper myristates; atomically disordered, crystalline copper stearates; atomically disordered, crystalline copper oleates; atomically disordered, crystalline copper gluconates; atomically disordered, crystalline copper glycolates; atomically disordered, crystalline copper adipates; atomically disordered, crystalline copper silicates; atomically disordered, crystalline copper phosphides; atomically disordered, crystalline copper halides; atomically disordered, crystalline copper hydrides, atomically disordered, crystalline copper nitrates; atomically disordered, crystalline copper carbonates; atomically disordered, crystalline copper sulfides; atomically disordered, crystalline copper sulfadiazines; atomically disordered, crystalline copper acetates; atomically disordered, crystalline copper lactates; atomically disordered, crystalline copper citrates; atomically disordered, crystalline copper benzoate; atomically disordered, crystalline copper methanesulfonate; atomically disordered, crystalline copper trifluoracetate; atomically disordered, crystalline copper trifluoromethanesulfonate; atomically disordered, crystalline copper behenate; atomically disordered, crystalline copper phthalate; atomically disordered, crystalline copper oxalate; atomically disordered, crystalline copper sulfonate; atomically disordered, crystalline copper thiosulphates (e.g., atomically disordered, crystalline sodium copper thiosulphate, atomically disordered, crystalline potassium copper thiosulphate)).

The metal-containing material can be used to treat, for example a human or an animal (e.g., a dog, a cat, a horse, a bird, a reptile, an amphibian, a fish, a turtle, a guinea pig, a hamster, a rodent, a cow, a pig, a goat, a primate, a monkey, a chicken, a turkey, a buffalo, an ostrich, a sheep, a llama).

Substrate Coatings

Examples of commercially available metal-containing materials include the Acticoat™ family of dressings (Smith & Nephew, Hull, UK), which are formed of antimicrobial, anti-inflammatory atomically disordered, nanocrystalline silver-containing material coated on one or more substrates. Such dressings include the Acticoat™ dressings, the Acticoat7™ dressings, the Acticoat™ moisture coating dressings, and the Acticoat™ absorbent dressings.

A coating of a metal-containing material (e.g., an antimicrobial, atomically disordered, nanocrystalline silver-containing material) can be formed on a substrate using a desired technique. In certain embodiments, the coating is formed by depositing the material on the substrate surface using chemical vapor deposition, physical vapor deposition, and/or liquid phase deposition. Exemplary deposition methods include vacuum evaporation deposition, arc evaporation deposition, reactive sputtering deposition, sputter deposition, magnetron sputter deposition and ion plating.

In some embodiments, the coating is prepared using physical vapor deposition. FIG. 1 shows a vapor deposition system 100 that includes a vacuum chamber 110, an energy source 120 (e.g., an electron beam source, an ion source, a laser beam, a magnetron source), a target 130 and a substrate 140. During operation, energy source 120 directs a beam of energy 122 to target 130, causing material 132 to be removed (e.g., by evaporation) from target 130 and directed to a surface 142 of substrate 140. At least a portion of the removed material 132 is deposited on surface 142.

In general, the values of the system parameters (e.g., the temperature of surface 142, the pressure of chamber 110, the angle of incidence of removed material 132 on surface 142, the distance between target 130 and surface 142) can be selected as desired. The temperature of surface 142 can be relatively low during the deposition process. For example, during the deposition process, the ratio of the temperature of substrate 140 to the melting point of the material forming target 130 (as determined in using Kelvin) can be about 0.5 or less (e.g., about 0.4 or less, about 0.35 or less, about 0.3 or less).

The pressure in chamber 110 can be relatively high. For example, vacuum evaporation deposition, electron beam deposition or arc evaporation, the pressure can be about 0.01 milliTorr or greater. For gas scattering evaporation (pressure plating) or reactive arc evaporation, the pressure in chamber 110 can be about 20 milliTorr or greater. For sputter deposition, the pressure in chamber 110 can be about 75 milliTorr or greater. For magnetron sputter deposition, the pressure in chamber 110 can be about 10 milliTorr or greater. For ion plating, the pressure in chamber 110 can be 200 milliTorr or greater.

The angle of incidence of removed material 132 on surface 142 ($\theta$) can be relatively low. For example, the angle of incidence of removed material 132 on surface 142 can be about 75° or less (e.g., about 60° or less, about 45° or less, about 30° or less).

The distance between target 130 and surface 142 can be selected based upon the values of the other system parameters. For example, the distance between target 130 and surface 142 can be about 250 millimeters or less (e.g., about 150 millimeters or less, 125 millimeters or less, about 100 millimeters or less, about 90 millimeters or less, about 80 millimeters or less, about 70 millimeters or less, about 60 millimeters or less, about 50 millimeters or less, about 40 millimeters or less).

As noted above, it is believed that, the metal-containing material, when contacted with an alcohol or water-based electrolyte, can be released into the alcohol or water-based electrolyte (e.g., as ions, atoms, molecules and/or clusters). It is also believed that the ability to release the metal (e.g., as atoms, ions, molecules and/or clusters) on a sustainable basis from a coating is generally dependent upon a number of factors, including coating characteristics such as composition, structure, solubility and thickness, and the nature of the environment in which the device is used. As the level of atomic disorder is increased, it is believed that the amount of metal species released per unit time increases. For example, a silver metal film deposited by magnetron sputtering at a ratio of substrate temperature to the target melting point of less than about 0.5 and a working gas pressure of about 0.93 Pascals (about seven milliTorr) releases approximately ⅓ of the silver ions that a film deposited under similar conditions, but at four Pascals (about 30 milliTorr), will release over 10 days. Coatings formed with an intermediate structure (e.g., lower pressure, lower angle of incidence etc.) have been observed to have metal (e.g., silver) release values intermediate to these values as determined by bioassays. In general, to obtain relatively slow release of the metal, the coating should have a relatively low degree of atomic disorder, and, to obtain relatively fast release of the metal, the coating should have a relatively high degree of atomic disorder.

For continuous, uniform coatings, the time for total dissolution is generally a function of coating thickness and the nature of the environment to which the coating is exposed. The release of metal is believed to increase approximately linearly as the thickness of the coating is increased. For example, it has been observed that a two fold increase in coating thickness can result in about a two fold increase in longevity.

In certain embodiments, it is possible to manipulate the degree of atomic disorder, and therefore the metal release from a coating, by forming a thin film coating with a modulated structure. For example, a coating deposited by magnetron sputtering such that the working gas pressure was relatively low (e.g., about two Pascals or about 15 milliTorr) for about 50% of the deposition time and relatively high (e.g., about four Pascals or 30 milliTorr) for the remaining time, can result in a relatively rapid initial release of metal (e.g., ions, clusters, atoms, molecules), followed by a longer period of slow release. This type of coating is can be particularly effective on devices such as urinary catheters for which an initial rapid release is advantageous to achieve quick antimicrobial concentrations followed by a lower release rate to sustain the concentration of metal (e.g., ions, clusters, atoms, molecules) over a period of weeks.

It is further believed that the degree of atomic disorder of a coating can be manipulated by introducing one or more dissimilar materials into the coating. For example, one or more gases can be present in chamber 110 during the deposition process. Examples of such gases include oxygen-containing gases (e.g., oxygen, air, water), nitrogen-containing gases (e.g., nitrogen, air), hydrogen-containing gases (e.g., water, hydrogen), boron-containing gases (e.g., boron), sulfur-containing gases (e.g., sulfur), carbon-containing gases (e.g., carbon monoxide, carbon dioxide), phosphorus-containing gases, silicon-containing gases, and halogen-containing gases (e.g., fluorine, chlorine, bromine, iodine). The additional gas(es) can be co-deposited or reactively deposited with material 132. This can result in the deposition/formation of an oxide, hydroxide, nitride, carbide, phosphide, silicate, boride, sulfide, hydride, nitrate, carbonate, alkali thiosulphate (e.g., sodium thiosulphate, potassium thiosulphate), myristate, sorbate, stearate, oleate, gluconate, glycolate, adipate, silicate, phosphide, sulfadiazine, acetate, lactate, citrate, benzoate, methanesulfonate, trifluoracetate, trifluoromethanesulfonate, behenate, phthalate, oxalate, sulfonate, and/or halide material (e.g., an oxide of a metal-containing material, a hydroxide of a metal-containing material, a nitride of a metal-containing material, a carbide of a metal-containing material, a phosphide of a metal-containing material, a silicate of a metal-containing material, a boride of a metal-containing material, a sulfide of a metal-containing material, a hydride of a metal-containing material, a halide of a metal-containing material, a nitrate of a metal-containing material, a carbonate of a metal-containing material, a myristate of a metal-containing material, a sorbate of a metal-containing material, a stearate of a metal-containing material, an oleate of a metal-containing material, a gluconate of a metal-containing material, a glycolate of a metal-containing material, an adipate of a metal-containing material, a silicate of a metal-containing material, a phosphide of a metal-containing material, a sulfide of a metal-containing material, a sulfadiazine of a metal-containing material, a sulfadiazine of a metal-containing material, an acetate of a metal-containing material, a lactate of a metal-containing material, a citrate of a metal-containing material, a benzoate of a metal-containing material, a methanesulfonate of a metal-containing material, a trifluoracetate of a metal-containing material, a trifluoromethanesulfonate of a metal-containing material, a behenate of a metal-containing material, a phthalate of a metal-containing material, a oxalate of a metal-containing material, a sulfonate of a metal-containing material, an alkali metal thiosulphate (e.g., sodium metal thiosulphate, potassium metal thiosulphate) of a metal-containing material). Without wishing to be bound by theory, it is believed that atoms and/or molecules of the additional gas(es) may become absorbed or trapped in the material, resulting in enhanced atomic disorder. The additional gas(es) may be continuously supplied during deposition, or may be pulsed to (e.g., for sequential deposition). In embodiments, the material formed can be constituted of a material with a ratio of material 132 to additional gas(es) of about 0.2 or greater. The presence of dissimilar atoms or molecules in the coating can enhance the degree of atomic disorder of the coating due to the difference in atomic radii of the dissimilar constituents in the coating. In some embodiments, one or more metals and/or non-metals can help preserve disorder, for example, by forming a barrier to atomic diffusion.

The presence of dissimilar atoms or molecules in the coating may also be achieved by co-depositing or sequentially depositing one or more additional metal elements (e.g., one or more additional antimicrobial metal elements). Such additional metal elements include, for example, Au, Pt, Ta, Ti, Nb, Zn, V, Hf, Mo, Si, Al, and other transition metal elements. It is believed that the presence of dissimilar metal elements (one or more primary metal elements and one or more additional metal elements) in the coating can reduce atomic diffusion and stabilize the atomically disordered structure of the coating. A coating containing dissimilar metal elements can be formed, for example, using thin film deposition equipment with multiple targets. In some embodiments, sequentially deposited layers of the metal elements are discontinuous (e.g., islands within the primary metal). In certain embodiments, the weight ratio of the additional metal(s) to the primary metal(s) is greater than about 0.2.

While FIG. 1 shows one embodiment of a deposition system, other embodiments are possible. For example, the deposition system can be designed such that during operation the substrate moves along rollers. Additionally or alternatively, the deposition system may contain multiple energy sources, multiple targets, and/or multiple substrates. The multiple energy sources, targets and/or substrates can be, for example, positioned in a line, can be staggered, or can be in an array.

In certain embodiments, two layers of the material are deposited on the substrate to achieve an optical interference effect. Alternatively, the two layers can be formed of different materials, with the outer (top) of the two layers being formed of an antimicrobial, atomically disordered, nanocrystalline silver-containing material, and the inner of the two layers having appropriate reflective properties so that the two layers can provide an interference effect (e.g., to monitor the thickness of the outer (top) of the two layers).

The substrate can be selected as desired. The substrate may be formed of one layer or multiple layers, which may be formed of the same or different materials. In certain embodiments, the substrate can include one or more layers containing a bioabsorbable material. Bioabsorbable materials are disclosed, for example, in U.S. Pat. No. 5,423,859. In general, bioabsorbable materials can include natural bioabsorbable polymers, biosynthetic bioabsorbable polymers and synthetic bioabsorbable polymers. Examples of synthetic bioabsorbable polymers include polyesters and polylactones (e.g., polymers of polyglycolic acid, polymers of glycolide, polymers of lactic acid, polymers of lactide, polymers of dioxanone, polymers of trimethylene carbonate, polyanhydrides, polyesteramides, polyortheoesters, polyphosphazenes, and copolymers of the foregoing). Examples of natural bioabsorbable polymers include proteins (e.g., albumin, fibrin, collagen, elastin), polysaccharides (e.g., chitosan, alginates, hyaluronic acid). Examples of biosynthetic polymers include polyesters (e.g., 3-hydroxybutyrate polymers).

In some embodiments, the substrate includes multiple layers (e.g., two layers, three layers, four layers, five layers, six layers, seven layers, eight layers, nine layers, 10 layers). The layers can be laminated together (e.g., by thermal fusing, stitching and/or ultrasonic welding).

One or more layers (e.g., an outer layer) of a multi-layer substrate can be formed of a perforated (and optionally nonadherent) material (e.g., a woven material or a non-woven material) that can allow fluid to penetrate or diffuse therethrough. Such materials include, for example, cotton, gauze, polymeric nets (e.g., polyethylene nets, nylon nets, polypropylene nets, polyester nets, polyurethane nets, polybutadiene nets), polymeric meshes (e.g., polyethylene meshes, nylon meshes, polypropylene meshes, polyester meshes, polyurethane meshes, polybutadiene meshes) and foams (e.g., an open cell polyurethane foam). Examples of commercially available materials include DELNET™ P530 non-woven polyethylene veil (Applied Extrusion Technologies, Inc., Middletown, Del.), Exu-Dry CONFORMANT2™ non-woven polyethylene veil (Frass Survival Systems, Inc., NY, N.Y.), CARELLE™ material (Carolina Formed Fabrics Corp.), NYLON90™ material (Carolina Formed Fabrics Corp.), N-TERFACE™ material (Winfield Laboratories, Inc., Richardson, Tex.), HYPOL™ hydrophilic polyurethane foam (W.R. Grace & Co., NY, N.Y.).

One or more layers (e.g., an inner layer) of a multi-layer substrate can be formed of an absorbent material (e.g., a woven material or a non-woven material) formed of, for example, rayon, polyester, a rayon/polyester blend, polyester/cotton, cotton and/or cellulosic fibers. Examples include creped cellulose wadding, air felt, air laid pulp fibers and gauze. An example of a commercially available material is SONATRA™ 8411 70/30 rayon/polyester blend (Dupont Canada, Mississauga, Ontario).

One or more layers (e.g., an outer layer) of a multi-layer substrate can be formed of an occlusive or semi-occlusive material, such as an adhesive tape or polyurethane film (e.g., to secure the device to the skin and/or to retain moisture).

In some embodiments, the layers in a multi-layer substrate are laminated together (e.g., at intermittent spaced locations) by ultrasonic welds. Typically, heat (e.g., generated ultrasonically) and pressure are applied to either side of the substrate at localized spots through an ultrasonic horn so as to cause flowing of at least one of the plastic materials in the first and second layers and the subsequent bonding together of the layers on cooling. The welds can be formed as localized spots (e.g., circular spots). The spots can have a diameter of about 0.5 centimeter or less.

The shape of the substrate can generally be varied as desired. For example, the substrate can be in the shape of a film, a fiber or a powder.

The substrate/coating article can be used in a variety of articles. For example, the article can be in the shape of a medical device. Exemplary medical devices include wound closure devices (e.g., sutures, staples, adhesives), tissue repair devices (e.g., meshes, such as meshes for hernia repair), prosthetic devices (e.g., internal bone fixation devices, physical barriers for guided bone regeneration, stents, valves, electrodes), tissue engineering devices (e.g., for use with a blood vessel, skin, a bone, cartilage, a liver), controlled drug delivery systems (e.g., microcapsules, ion-exchange resins) and wound coverings and/or fillers (e.g., alginate dressings, chitosan powders). In some embodiments, the article is a transcutaneous medical device (e.g., a catheter, a pin, an implant), which can include the substrate/coating supported on, for example, a solid material (e.g., a metal, an alloy, latex, nylon, silicone, polyester and/or polyurethane). In some embodiments, the article is in the form of a patch (e.g., a patch having an adhesive layer for adhering to the skin, such as a transdermal patch).

Subsequent to deposition, the material can optionally be annealed. In general, the anneal is conducted under conditions to increase the stability (e.g., shelf life) of the material while maintaining the desired therapeutic activity of the material. In certain embodiments, the material can be annealed at a temperature of about 200° C. or less (e.g., about room temperature).

The substrate/coating is typically sterilized prior to use (e.g., without applying sufficient thermal energy to anneal out the atomic disorder). The energy used for sterilization can be, for example, gamma radiation or electron beam radiation. In some embodiments, ethylene oxide sterilization techniques are used to sterilize the substrate/coating.

Free Standing Powders

A free standing powder can be prepared by, for example, cold working or compressing to impart atomic disorder to the powder. In certain embodiments, a free standing powder is prepared by forming a coating of the material as described above, and then removing the material from the surface of the substrate. For example, the material can be scraped from the surface of the substrate by one or more scrapers. In embodiments in which the substrate moves during deposition of the material, the scrapers can remove the material as the substrate moves. The scrapers can be, for example, suspended above the substrate. Such scrapers can be, for example, weighted and/or spring loaded to apply pressure sufficient to remove the material as the substrate moves. In some embodiments (e.g., when a continuous belt is used), the scrapers can be located above the end rollers to remove the material with a reverse dragging action as the substrate rounds the end roller.

A free standing powder can be used to treat a condition in various ways. As an example, the powder can sprinkled onto the subject's skin. As another example, the powder can be inhaled using an inhaler, such as a dry powder inhaler. In some embodiments, a dry powder can be in the form of an aerosol, which contains, for example, at least about 10 (e.g., at least about 20, or at least about 30) weight percent and/or at most about 99 (e.g., at most about 90, at most about 80, at most about 70, at most about 60, or at most about 50) weight percent of the dry powder. In some embodiments, the aerosol can contain from about 10 to 99 (e.g., from 10 to 90, from 10 to 70, from 10 to 50) percent by weight of the dry powder.

In certain embodiments (e.g., when the free standing powder is inhaled), the average particle size of the free standing powder is selected to reduce the likelihood of adverse reaction(s) of the particles in the tissue and/or to deposit the powder onto specific anatomical locations (e.g., tissue contacted by the free standing powder during inhalation). In some embodiments, the average particle size is selected (e.g., less than about 10 microns) so that a relatively small amount of the particles get into the lower respiratory tract. In embodiments, a free standing powder can have an average particle size of less than about 10 microns (e.g., less than about eight microns, less than about five microns, less than about two microns, less than about one micron, less than about 0.5 micron) and/or at least about 0.01 micron (e.g., at least about 0.1 micron, or at least about 0.5 micron).

Powder Impregnated Materials

The metal-containing material can be in the form of a powder impregnated material. Such powder impregnated materials can, for example, be in the form of a hydrocolloid having the free standing powder blended therein. A powder impregnated material can be, for example, in the form of a dressing, such as a hydrocolloid dressing.

The following examples are illustrative and not intended as limiting.

EXAMPLE 1

Preparation of Nanocrystalline Silver Coatings on Dressings

This example shows the preparation of a bilayer nanocrystalline silver coating on a dressing material. A high density polyethylene dressing, DELNET™ or CONFORMANT 2™ was coated with a silver base layer and a silver/oxide top layer to generate a colored anti-microbial coating having indicator value. The coating layers were formed by magnetron sputtering under the conditions set out in the following table.

| Sputtering Conditions: | Base Layer | Top Layer |
|---|---|---|
| Target | 99.99% Ag | 99.99% Ag |
| Target Size | 20.3 cm diameter | 20.3 cm diameter |
| Working Gas | 96/4 wt % Ar/$O_2$ | 96/4 wt % Ar/$O_2$ |
| Working Gas Pressure | 5.33 Pa (40 mT) | 5.33 Pa (40 mT) |
| Power | 0.3 kW | 0.15 kW |
| Substrate Temperature | 20° C. | 20° C. |
| Base Pressure | $3.0 \times 10^{-6}$ Torr | $3.0 \times 10^{-6}$ Torr |
| Anode/Cathode Distance | 100 mm | 100 mm |
| Sputtering Time | 7.5-9 min | 1.5 min |
| Voltage | 369-373 V | 346 V |

The resulting coating was blue in appearance. A fingertip touch was sufficient to cause a color change to yellow. The base layer was about 900 nm thick, while the top layer was 100 nm thick.

To establish that silver species were released from the coated dressings, a zone of inhibition test was conducted. Mueller Hinton agar was dispensed into Petri dishes. The agar plates were allowed to surface dry prior to being inoculated with a lawn of *Staphylococcus aureus* ATCC#25923. The inoculant was prepared from Bactrol Discs (Difco, M.), which were reconstituted as per the manufacturer directions. Immediately after inoculation, the coated materials to be tested were placed on the surface of the agar. The dishes were incubated for 24 hr. at 37° C. After this incubation period, the zone of inhibition was calculated (corrected zone of inhibition=zone of inhibition−diameter of the test material in contact with the agar). The results showed a corrected ZOI of about 10 mm, demonstrating good release of silver species.

The coating was analyzed by nitric acid digestion and atomic absorption analysis to contain 0.24+/−0.04 mg silver per mg high density polyethylene. The coating was a binary alloy of silver (>97%) and oxygen with negligible contaminants, based on secondary ion mass spectroscopy. The coating, as viewed by SEM, was highly porous and consisted of equiaxed nanocrystals organized into coarse columnar structures with an average grain size of 10 nm. Silver release studies in water demonstrated that silver was released continuously from the coating until an equilibrium concentration of about 66 mg/L was reached (determined by atomic absorption), a level that is 50 to 100 times higher than is expected from bulk silver metal (solubility 1 mg/L).

By varying the coating conditions for the top layer to lengthen the sputtering time to 2 min, 15 sec., a yellow coating was produced. The top layer had a thickness of about 140 nm and went through a color change to purple with a fingertip touch. Similarly, a purple coating was produced by shortening the sputtering time to 1 min, to achieve a top layer thickness of about 65 nm. A fingertip touch caused a color change to yellow.

To form a three layer dressing, two layers of this coated dressing material were placed above and below an absorbent core material formed from needle punched rayon/polyester (SONTARA™ 8411). With the silver coating on both the first and third layers, the dressing may be used with either the blue coating side or the silver side in the skin facing position. For indicator value, it might be preferable to have the blue coating visible. The three layers were laminated together by ultrasonic welding to produce welds between all three layers spaced at about 2.5 cm intervals across the dressing. This allowed the dressing to be cut down to about 2.5 cm size portions for smaller dressing needs while still providing at least one weld in the dressing portion.

The coated dressings were sterilized using gamma radiation and a sterilization dose of 25 kGy. The finished dressing was packaged individually in sealed polyester peelable pouches, and has shown a shelf life greater than 1 year in this form. The coated dressings can be cut in ready to use sizes, such as 5.1×10.2 cm strips, and slits formed therein before packaging. Alternatively, the dressings may be packaged with instructions for the clinician to cut the dressing to size and form the desired length of the slit for the medical device.

Additional silver coated dressings were prepared in a full scale roll coater under conditions to provide coatings having the same properties set out above, as follows:

the dressing material included a first layer of silver coated DELNET, as set out above, laminated to STRATEX, AET, 8.0N$P_2$-A/QW, which is a layer of 100% rayon on a polyurethane film.

Silver Foam Dressing—three layers of silver coated high density polyethylene prepared as above, alternating with two layers of polyurethane foam, L-00562-6 Medical Foam, available from Rynel Ltd., Bootbay, Me., USA.

EXAMPLE 2

Preparation of Nanocrystalline Silver Powders

Nanocrystalline silver powder was prepared by preparing silver coatings on silicon wafers, under the conditions set forth in the table above, and then scraping the coating off using a glass blade.

Nanocrystalline silver powder was also prepared by sputtering silver coatings on silicon wafers using Westaim Biomedical NGRC unit, and then scraping the coating off.

The sputtering conditions were as follows:

| | |
|---|---|
| Target: | 99.99% Ag |
| Target Size: | 15.24 cm × 1216.125 cm |
| Working Gas: | 75:25 wt % Ar/$O_2$ |
| Working Gas Pressure: | 40 mTorr |
| Total Current: | 40 A |
| Base Pressure: | $5.0 \times 10^{-5}$ Torr |
| Sandvik Belt Speed: | 340 mm/min |
| Voltage: | 370 V |

The powder has a particle size ranging from 2 μm to 100 μm, with crystallite size of 8 to 10 nm, and demonstrated a positive rest potential.

EXAMPLE 3

Preparation of Nanocrystalline Silver Coating on HDPE Mesh

The silver coated mesh was produced, as set forth in Example 1, by sputtering silver onto Delnet, a HDPE mesh (Applied Extrusion Technologies, Inc., Middletown, Del., USA) using Westaim Biomedical TMRC unit under the following conditions:

| | |
|---|---|
| Target: | 99.99% Ag |
| Target Size: | 15.24 cm × 152.4 cm |

-continued

| | |
|---|---|
| Working Gas: | 99.375:0.625 wt % Ar/O$_2$ |
| Working Gas Pressure: | 5.33 Pascals (40 mTorr) |
| Total Current: | 22 A |
| Base Pressure: | $5.0 \times 10^{-5}$ Torr |
| Sandvik Belt Speed: | 577 mm/min |
| Voltage: | 367 V |

The coating was tested and found to have a weight ratio of reaction product to silver of between 0.05 and 0.1. The dressing was non-staining to human skin.

EXAMPLE 4

Preparation of Atomic Disordered Nanocrystalline Silver Powders

Nanocrystalline silver coatings were prepared by sputtering silver in an oxygen-containing atmosphere directly onto an endless stainless steel belt of a magnetron sputtering roll coater, or onto silicon wafers on the belt. The belt did not need to be cooled. The coatings were scraped off with the belt with suspended metal scrapers as the belt rounded the end rollers. For the coated silicon wafers, the coatings were scraped off with a knife edge. The sputtering conditions were as follows:

| | |
|---|---|
| Target: | 99.99% Ag |
| Target Size: | 15.24 cm × 1216.125 cm |
| Working Gas: | 75:25 wt % Ar/O$_2$ |
| Working Gas Pressure: | 5.33 Pascals (40 milliTorr) |
| Total Current: | 40 A |
| Base Pressure: | $5.0 \times 10^{-5}$ Torr (range: $1 \times 10^{-4}$-$9 \times 10^{-7}$ Torr or $1 \times 10^{-2}$-$1.2 \times 10^{-4}$ Pa) |
| Sandvik Belt Speed: | 340 mm/min |
| Voltage: | 370 V |

Note -
pressure conversions to Pa herein may not be accurate, most accurate numbers are in ton, mTorr units.

The powder had a particle size ranging from 2 μm to 100 μm, with grain or crystallite size of 8 to 10 nm (i.e., nanocrystalline), and demonstrated a positive rest potential.

Similar atomic disordered nanocrystalline silver powders were formed as set forth hereinabove by magnetron sputtering onto cooled steel collectors, under conditions taught in the prior Burrell et al. patents to produce atomic disorder.

EXAMPLE 5

Silver Compositions for Treatment of Sporulating Bacterial Conditions

The activities of different forms of silver (e.g., silver nitrate, silver (I) oxide, and a nanocrystalline silver produced by physical vapor deposition by magnetron sputtering) were assessed against the spores and vegetative cells of five strains of *C. difficile*. The in vivo efficacy of silver against CDAD was also studied. Efficacy against vegetative cells of *C. difficile* was ascertained by anaerobic MIC assay. Sporicidal activity was determined by exposing spores to test agents for intervals ranging from 15-120 minutes. Six days of negative culture were taken as an indication of sporicidal activity. The ability of silver to prevent CDAD was determined by orally administering silver dispersions or control antibiotics to hamsters previously colonized with *C. difficile*, after pre-exposure to clindamycin. The silver MICs against vegetative cells of *C. difficile* ranged from 8-23 μg/ml, which was significantly lower ($p=0.024$ by Mann-Whitney) than MICs obtained against other tested anaerobic species. Silver had sporicidal activity that required at least 15 minutes exposure to a solution and/or nanodispersion of 50-500 μg/ml. In vivo studies demonstrated that a single oral dose of silver reduced colonization by *C. difficile* to an extent similar to a single oral dose of metronidazole, but not as well as a single oral dose of vancomycin ($p<0.05$ by Kruskal-Wallis, Tukey test). Additionally, multiple doses of nanocrystalline silver decreased the rate of progression of CDAD in hamsters, and reduced the incidence of CDAD when delivered prophylactically. Pre-exposure of hamsters to nanocrystalline silver did not render hamsters susceptible to CDAD. These data show that silver is bactericidal and sporicidal against *C. difficile*, and can be used as a first-line treatment, or as prophylaxis, for CDAD.

Materials & Methods

Bacterial Culture

*C. difficile* isolates 5340 and 1459, and strains 43594, 43596, and 43600 were cultured at 37° C. on *Clostridium* Reinforced Agar (Remel) or Columbia Blood Agar (Remel) in an atmosphere of 80% $N_2$, 10% $CO_2$, 10% $H_2$. Bacteria were resuspended in Brain Heart Infusion for assays (BHI).

Silver

Silver nitrate and silver oxide were obtained from Sigma (St. Louis, Mo.). Nanocrystalline silver was 96.1% silver with a crystallite size <200 nm. For broth microdilution Minimal Inhibitory Concentration assays and Sporicidal assays, silver was prepared either in water as a nanodispersion with lecithin or PVA present as a dispersant, or as a solution in 0.1 M Lactate buffer, pH 4.0. Silver preparations were filtered at 0.2 microns and stored in the dark at room temperature.

Microdilution MIC Assay

Preparations of silver were serially diluted in BHI, and then inoculated with bacterial suspension containing approx $10^6$ CFU. Plates were incubated 48-72 hours at 37° C. and growth was assessed by measuring the optical density of the cultures at 625 nm, or by visual inspection.

Sporicidal Assay

Spore germination was induced as previously described in, for example, Haraldsen J D and Sonenshein A L. Mol Microbiol. 2003 48(3): 811-821; and Ionesco H. C R Acad Sci Hebd Seances Acad Sci D. 1978 Sep. 25; 287(6):659-61. *C. difficile* suspended in BHI was heat-killed at 80° C. for 10 minutes, and germination then stimulated by a 30-min incubation at 50° C. in the presence of 165 μM thioglycollate, followed by a 15-min incubation at 37° C. in the presence of 4 mg/ml lysozyme. The spores were then incubated in the presence of silver or glutaraldehyde (each also diluted in BHI), and at timepoints 10-μl aliquots were removed, diluted 1:1000 in fresh BHI, and subcultured for 5-6 days to determine viability.

In Vivo Model of *C. difficile* Associated Disease

Hamsters received one dose of clindamycin orogastrically (10 mg/kg). In some experiments, the hamsters were inoculated orogastrically with $10^3$-$10^4$ *C. difficile* spores one day after exposure to clindamycin. In other experiments, no spores were given and the Clindamycin-treated hamsters were allowed to acquire infection from their environment. To assess colonization, three fecal pellets were collected from each hamster, and the pellets were solubilized in sterile PBS or ethanol and then swabbed onto *C. difficile*-selective agar and cultured anaerobically at 36° C. for 24-28 hours. Colonization was considered positive when feces yielded colonies with typical *C. difficile* morphology that fluoresced green under UV light. Colonized hamsters were assigned to treatment groups that received orogastric treatment with nanocrystalline silver (40-120 mg/kg/day), placebo suspension, or vancomycin (25 mg/kg/day). Prophylactic treatments were given once per day for three days prior to, and on, the day of clindamycin treatment.

Results

Both microcrystalline and nanocrystalline silver exhibited antimicrobial activity against the vegetative cells of *C. difficile* and/or *C. perfringens* (Table 1A). Silver was also tested against other aerobic or facultative organisms. The MIC values for inhibition of the vegetative growth of *C. difficile* was higher than for aerobic or facultative organisms, but slightly lower than for other anaerobes.

TABLE 1A

Antimicrobial Potency of Silver Versus *Clostridium* bacteria. MIC values in ppm (μg/ml), measured by standard broth microdilution MIC assays. Values shown are Median (Range).

| | Lactate preparation | |
|---|---|---|
| Species | Nano-Ag | $AgNO_3$ |
| *C. perfringens* | 85 | 92 |
| *C. difficile* | 17 (9-21) | 18 (8-23) |

Since nanocrystalline silver is shown to have sporicidal activity against the spores of *C. difficile*, its activity against spores of other bacteria is also of interest. *Bacillus cereus* is a close relative of the bacterium *Bacillus anthracis*, the cause of anthrax. Spores of *B. cereus* were treated with nanocrystalline silver, placebo, or Betadine (a positive control antiseptic). The results shown in Table 3 show that nanocrystalline silver reduces spore count by about ten fold relative to placebo and betadine under two different test conditions, 37 or 43 degrees Celsius.

TABLE 3

Viable spore counts of *Bacillus cereus* after overnight exposure to nanocrystalline silver or positive control Betadine.

| | 37° C. | 43° C. |
|---|---|---|
| Nano crystalline Ag | none detected | 100* |
| Placebo | 900 | 1100 |
| Betadine | 1100 | 600 |

*100 spores was the lower limit of quantitation.

Oral silver preparations also increased in a hamster model of CDAD. For example, when delivered in multiple doses, nanocrystalline silver caused a decrease in the rate of pro-

TABLE 1

Microdilution MIC values (in ppm) for *C. difficle* isolates 5340 and 1459. Nanocrystalline silver (nano Ag), silver nitrate, and silver (I) oxide were tested as solutions in lactate buffer, and as nanodispersions in PVA and Lecithin. n.i. = no inhibition was observed.

| | Lactate pH 4 | | | | PVA | | | | Lecithin | | | |
|---|---|---|---|---|---|---|---|---|---|---|---|---|
| | Nano Ag | $AgNO_3$ | $Ag_2O$ | none | Nano Ag | $AgNO_3$ | $Ag_2O$ | none | Nano Ag | $AgNO_3$ | $Ag_2O$ | none |
| 5340 | 17 | 18 | 16 | n.i. | 43 | 34 | 55 | n.i. | 27 | 9 | 26 | n.i. |
| 1459 | 9 | 9 | 31 | n.i. | 21 | 9 | 27 | n.i. | 13 | 9 | 26 | n.i. |

Silver nitrate, silver oxide, and nanocrystalline silver inactivated the spores of *C. difficile* (Table 2). Silver inactivated *C. difficile* spores at concentrations comparable to, or lower than, the concentration of glutaraldehyde needed to inactivate spores. The exposure time needed for silver's sporicidal activity was 1-2 hours (15, 30, and 45 min exposure was ineffective; data not shown), which was similar to the exposure time needed for glutaraldehyde.

TABLE 2

Sporicidal Activity of Silver Compared to Glutaraldehyde. Experiments were conducted with *C. difficile* strain ATCC 43596. Results indicated the presence (+) or absence (−) of growth after 5-6 days of subculture.

| Expt # | Conc. | Glutaraldehyde | $AgNO_3$ solution | $Ag_2O$ solution | Nanocrystalline Ag nanodispersion |
|---|---|---|---|---|---|
| 1 | 2% | − | | | |
| | 0.2% | − | | | |
| | 0.02% | + | | | |
| 2 | 0.05% | | − | | − |
| | 0.005% | | − | | − |
| | 0.0005% | | − | | − |
| | 0.00005% | | + | | + |
| 3 | 0.03% | | − | − | − |
| | 0.01% | | − | − | + | gression of CDAD in hamsters (FIG. 2) and this effect was dose-responsive (FIG. 3). Nanocrystalline silver reduced the incidence of CDAD when delivered prophylactically in multiple once/day doses prior to clindamycin administration (FIG. 4). Despite its broad-spectrum antimicrobial activity, nanocrystalline silver treatment did not predispose hamsters to the onset of CDAD (0% colonization).

The action of silver against the vegetative cells and spores of *C. difficile* in vitro, the preliminary efficacy data in a hamster model of CDAD, and the ability of silver to protect against the acquisition of disease opens the possibility of using silver as a preventive measure in high-risk populations (e.g., individuals having extended hospitalization, with advanced age, having exposure to any of a number of antibiotics, immuno-suppressed individuals, individuals having IBD, individuals having CDAD or having had CDAD, individuals undergoing chemotherapy), or of using silver in combination with metronidazole or vancomycin to decrease the likelihood of relapse. Further, as CDAD is a disease of the proximal large colon, with the possibility of the small intestine serving as a bacterial reservoir, treatments can be delivered orally, for example, in the form of a controlled-release formulation.

EXAMPLE 6

Controlled-Release Beads

Nanocrystalline silver was prepared as an aqueous nanodispersion containing 1% nanocrystalline silver, and this nanodispersion was sprayed onto sugar beads (CHR Hansen 18-20 mesh sugar spheres) using a Schlick spray gun fitted with a 1.0-mm nozzle, and operating at an atomizing pressure of 20 psi. Silver was sprayed onto the beads until the beads reached a 1.7% weight gain. The silver was then covered with Acryl-EZE MP controlled-release coating. The following two tables present analytical data on the silver-coated beads:

Analytical Data

Nanocrystalline silver coated beads were analyzed for total silver assay via Flame Atomic Absorption Spectrometry. Samples were analyzed in duplicate. The results are presented in Table 4 below.

TABLE 4

| Sample ID | Total Silver (mg/g) | Total Silver (% Ag) | Observations |
| --- | --- | --- | --- |
| Acryl-EZE MP and silver coated sugar bead | 0.55 | 0.055 | Small, round, brown beads |
| Non-Acryl-EZE MP coated silver sugar bead | 0.86 | 0.086 | Small, round, dark brown beads |
| 18-mesh sugar bead | <LOQ | <LOQ | Small, round, white beads |

Limit of Quantitation (LOQ) = 0.001% Ag

A controlled-release composition was prepared by vortexing 2 grams of Acryl-EZE MP- and silver-coated sugar bead of Table 3 in 9 mL of high-purity water and removing the supernatant for analysis. The theoretical total silver concentration of this sample would be 122.2 mg/L (see below for calculations).

Mass of Beads=2 grams

Silver concentration on Beads=0.55 mg/g (see Table 4)

Volume of $H_2O$=0.009 liters (2 grams*0.55 mg Ag/g)/0.009 liters=122.2 mg/L

The controlled-release composition was analyzed in duplicate for total silver assay via Flame Atomic Absorption Spectrometry. The results are presented in Table 5 below.

TABLE 5

| Sample ID | Total silver (mg/L) | Measured/ Theoretical | Observations |
| --- | --- | --- | --- |
| Acryl-EZE MP and silver coated sugar bead | 91.0 | 74.4% | Cloudy, brown/orange liquid |

To verify that the silver coated onto the beads was elutable and microbiologically active, the silver from a sample of beads eluted into deionized water was measured, and the eluate was used in a standard microdilution MIC assay. The eluate had the following silver MIC values: *Pseudomonas aeruginosa* 11 ug/ml, *Escherichia coli* 5 ug/ml, *Staphylococcus aureus* 6 ug/ml, *Clostridium difficile* 11 ug/ml. These values were comparable to the MIC values typically obtained against these bacterial species. Thus, the silver coated onto these beads had a normal level of antimicrobial activity.

The contents of U.S. patent application Ser. No. 11/766,891, filed Jun. 22, 2007; U.S. patent application Ser. No. 11/766,897, filed Jun. 22, 2007; U.S. patent application Ser. No. 11/766,902, filed Jun. 22, 2007, and Ser. No. 11/766,906, filed Jun. 22, 2007 are hereby incorporated by reference. All references, such as patent applications, publications, and patents, referred to herein are incorporated by reference in their entirety.

Other embodiments are in the claims.

What is claimed is:

1. A method, comprising:
    contacting an area of a subject with a nanocrystalline silver-containing material, and
    killing bacterial spores in the area with the nanocrystalline silver-containing material.

2. The method of claim 1, wherein the bacterial spores are selected from the group consisting of *Clostridium difficile* spores, *Clostridium perfringens* spores, *Clostridium tetani* spores, *Clostridium botulinum* spores, *Bacillus cereus* spores, *Bacillus anthracis* spores, and combinations thereof.

3. The method of claim 1, wherein the area of the subject further comprises a sporulating bacterial infection.

4. The method of claim 3, wherein the sporulating bacterial infection comprises a *Clostridium* infection.

5. The method of claim 4, wherein the *Clostridium* infection is selected from the group consisting of *Clostridium difficile* infection, *Clostridium perfringens* infection, *Clostridium tetani* infection, and *Clostridium botulinum* infection.

6. The method of claim 3, wherein the sporulating bacterial infection comprises a *Clostridium difficile* infection.

7. The method of claim 3, wherein the sporulating bacterial infection comprises a *Bacillus* infection.

8. The method of claim 7, wherein the sporulating *Bacillus* infection is selected from the group consisting of *Bacillus cereus* infection and *Bacillus anthracis* infection.

9. The method of claim 1, further comprising contacting the area with a non-metal antibiotic medication.

10. The method of claim 9, wherein the non-metal antibiotic medication is selected from the group consisting of vancomycin, metronidazole, benzoxazinorifamycin, rifaximin, and combinations thereof.

11. The method of claim 10, wherein the non-metal antibiotic medication is vancomycin.

12. The method of claim 10, wherein the non-metal antibiotic medication is metronidazole.

13. The method of claim 9, wherein the non-metal antibiotic medication is contacted to the area after contacting the area with the nanocrystalline silver-containing material.

14. The method of claim 9, wherein the non-metal antibiotic medication is contacted to the area before contacting the area with the nanocrystalline silver-containing material.

15. The method of claim 9, wherein the non-metal antibiotic medication is contacted to the area simultaneously with the nanocrystalline silver-containing material.

16. The method of claim 1, wherein the nanocrystalline silver-containing material is contacted with the area at a dose of from 0.1 to 1000 mg/kg of a subject.

17. The method of claim 1, wherein the nanocrystalline silver-containing material is contacted with the area at a dose of from 0.1 to 10,000 mg.

18. The method of claim 1, wherein the nanocrystalline silver-containing material is contacted with the area at a frequency of from one to four times per day.

19. The method of claim 9, wherein the non-metal antibiotic medication is contacted with the area at a dose of from 50 to 4000 mg/kg of a subject.

20. The method of claim 9, wherein the non-metal antibiotic medication is contacted with the area at a dose of from 50 to 4000 mg.

21. The method of claim 9, wherein the non-metal antibiotic medication is contacted with the area at a frequency of from one to four times per day.

22. The method of claim 1, wherein the area is selected from the group consisting of an oral cavity, a gastrointestinal tract, a nasal cavity, a respiratory tract, an ulceration, a connective tissue, and a wound.

23. The method of claim 1, wherein the nanocrystalline silver-containing material is in a form selected from the group consisting of a solution, a nanodispersion, an aerosol, a cream, and a gel.

24. The method of claim 1, wherein the nanocrystalline silver-containing material is in the form of a controlled-release composition.

25. The method of claim 24, wherein the controlled-release composition is selected form the group consisting of a suspension, a capsule, a tablet, and a pill.

26. The method of claim 24, wherein the controlled-release composition comprises a bead comprising the nanocrystalline silver-containing material, wherein the bead has a maximum average dimension of from 0.5 to 2 mm.

27. The method of claim 26, wherein the bead comprises from 0.01 to 20 percent by weight of the nanocrystalline silver-containing material.

28. The method of claim 26, wherein the bead is coated with the nanocrystalline silver-containing material.

29. The method of claim 27, wherein the bead further comprises a controlled-release coating.

30. The method of claim 26, wherein the bead comprises sugar or starch.

31. The method of claim 1, wherein contacting the area with the nanocrystalline silver-containing material comprises oral administration of the nanocrystalline silver-containing material.

32. The method of claim 1, wherein contacting the area with the nanocrystalline silver-containing material comprises rectal administration of the nanocrystalline silver-containing material.

33. The method of claim 1, wherein contacting the area with the nanocrystalline silver-containing material comprises inhalation of the nanocrystalline silver-containing material.

34. The method of claim 1, wherein contacting the area with the nanocrystalline silver-containing material comprises topical administration of the nanocrystalline silver-containing material.

35. An article, comprising:
a bead comprising from 0.01 to 20 percent by weight of a metal-containing material; and
a controlled-release coating on the bead,
wherein the bead has a maximum average dimension of from 0.5 to 2 mm.

36. The article of claim 35, wherein the metal-containing material comprises an atomically disordered metal-containing material.

37. The article of claim 35, wherein the metal-containing material is selected from the group consisting of silver-containing materials, gold-containing materials, platinum-containing materials, palladium-containing materials, copper-containing materials, zinc-containing materials, and combinations thereof.

38. The article of claim 35, wherein the metal-containing material comprises an atomically disordered, nanocrystalline metal-containing material.

39. The article of claim 35, wherein the metal-containing material comprises a nanocrystalline silver.

40. The article of claim 35, wherein the metal-containing material comprises an atomically disordered, nanocrystalline silver.

41. The article of claim 35, wherein the metal-containing material comprises silver oxide.

42. The article of claim 35, wherein the bead further comprises a material selected from the group consisting of sugar, starch, and combination thereof.

43. The article of claim 35, wherein the article comprises from 0.01 to 20 percent by weight of the controlled-release coating.

44. The article of claim 35, wherein the controlled-release coating comprises a material selected from the group consisting of beeswax, beeswax and glyceryl monostearate, shellac and cellulose, cetyl alcohol, mastic and shellac, shellac and stearic acid, polyvinyl acetate and ethyl cellulose, neutral copolymer of polymethacrylic acid ester (Eudragit L30D), copolymer of methacrylic acid and methacrylic acid methylester (Eudragits), neutral copolymers of polymethacrylic acid esters containing metallic stearates, neutralized hydroxypropyl methylcellulose phthalate polymer, and combinations thereof.

45. The article of claim 35, wherein the article is selected from the group consisting of a suspension, a capsule, a tablet, and a pill.

* * * * *

UNITED STATES PATENT AND TRADEMARK OFFICE
CERTIFICATE OF CORRECTION

PATENT NO. : 8,425,880 B1
APPLICATION NO. : 12/109897
DATED : April 23, 2013
INVENTOR(S) : Jeffrey B. Lyczak et al.

Page 1 of 3

It is certified that error appears in the above-identified patent and that said Letters Patent is hereby corrected as shown below:

In the Specifications:

Column 1, Line 48
Delete "enterophathogenic" and insert - - enteropathogenic - - therefor.

Column 19, Line 1
Delete "xantham" and insert - - xanthan - - therefor.

Column 21, Line 59
Delete "100" and insert - - 100 µg - - therefor.

Column 26, Line 11
Delete "Color Quest" and insert - - ColorQuest - - therefor.

Column 30, Line 2
Delete "trifluoracetate," and insert - - trifluoroacetate, - - therefor.

Column 30, Line 19-20
Delete "trifluoracetate," and insert - - trifluoroacetate, - - therefor.

Signed and Sealed this
Sixteenth Day of July, 2013

Teresa Stanek Rea
*Acting Director of the United States Patent and Trademark Office*

CERTIFICATE OF CORRECTION (continued)
U.S. Pat. No. 8,425,880 B1

Column 32, Line 47
Delete "trifluoracetate," and insert -- trifluoroacetate, -- therefor.

Column 32, Line 66
Delete "trifluoracetate," and insert -- trifluoroacetate, -- therefor.

Column 33, Line 20
Delete "trifluoracetate," and insert -- trifluoroacetate, -- therefor.

Column 33, Line 42
Delete "trifluoracetate," and insert -- trifluoroacetate, -- therefor.

Column 33, Line 62
Delete "trifluoracetate," and insert -- trifluoroacetate, -- therefor.

Column 34, Line 13
Delete "trifluoracetate," and insert -- trifluoroacetate, -- therefor.

Column 34, Line 25
Delete "trifluoracetate," and insert -- trifluoroacetate, -- therefor.

Column 34, Line 51
Delete "trifluoracetate," and insert -- trifluoroacetate, -- therefor.

Column 35, Line 4
Delete "trifluoracetate," and insert -- trifluoroacetate, -- therefor.

Column 35, Line 27
Delete "trifluoracetate," and insert -- trifluoroacetate, -- therefor.

Column 35, Line 50-51
Delete "trifluoracetate," and insert -- trifluoroacetate, -- therefor.

Column 36, Line 5
Delete "trifluoracetate," and insert -- trifluoroacetate, -- therefor.

Column 36, Line 23
Delete "trifluoracetate," and insert -- trifluoroacetate, -- therefor.

Column 36, Line 56
Delete "trifluoracetate;" and insert -- trifluoroacetate; -- therefor.

Column 37, Line 20-21
Delete "trifluoracetate;" and insert -- trifluoroacetate; -- therefor.

Column 37, Line 54
Delete "trifluoracetate;" and insert -- trifluoroacetate; -- therefor.

Column 38, Line 22
Delete "trifluoracetate;" and insert -- trifluoroacetate; -- therefor.

Column 38, Line 54
Delete "trifluoracetate;" and insert -- trifluoroacetate; -- therefor.

Column 39, Line 17 (Approx.)
Delete "trifluoracetate;" and insert -- trifluoroacetate; -- therefor.

Column 41, Line 31
Delete "trifluoracetate," and insert -- trifluoroacetate, -- therefor.

Column 41, Line 54
Delete "trifluoracetate" and insert -- trifluoroacetate -- therefor.

Column 42, Line 55
Delete "polyortheoesters," and insert -- polyorthoesters, -- therefor.

Column 43, Line 13
After "Inc.," delete "NY,".

Column 43, Line 18
After "Co.," delete "NY,".

Column 45, Line 50
Delete "1 mg/L)." and insert -- ≤1 mg/L). -- therefor.

Column 46, Line 24
Delete "Bootbay," and insert -- Boothbay, -- therefor.

Column 50, 17 (Approx.) (TABLE 3)
Delete "Nano crystalline" and insert -- Nanocrystalline -- therefor.